US005736387A

United States Patent [19]
Paul et al.

[11] Patent Number: 5,736,387
[45] Date of Patent: Apr. 7, 1998

[54] ENVELOPE FUSION VECTORS FOR USE IN GENE DELIVERY

[75] Inventors: Ralph W. Paul; Robert Overell, both of Seattle, Wash.

[73] Assignee: Targeted Genetics Corporation, Seattle, Wash.

[21] Appl. No.: 244,469

[22] PCT Filed: Jun. 1, 1995

[86] PCT No.: PCT/US94/06128

§ 371 Date: Jun. 1, 1994

§ 102(e) Date: Jun. 1, 1994

[87] PCT Pub. No.: WO94/27643

PCT Pub. Date: Dec. 8, 1994

Related U.S. Application Data

[63] Continuation-in-part of Ser. No. 70,117, Jun. 1, 1993, abandoned.

[51] Int. Cl.⁶ .................................................. C12N 15/63
[52] U.S. Cl. .................. 435/320.1; 435/325; 435/69.7; 435/69.5; 435/69.51; 435/69.52; 435/91.2; 435/6; 424/93.21; 514/44; 530/387.1; 530/350; 536/23.5; 536/24.31
[58] Field of Search ........................ 514/44; 424/93.21, 424/69.51, 69.52; 435/320.1, 6, 91.7, 325, 69.7, 69.52, 69.1, 69.5, 69.51, 91.2; 530/387.1, 350; 536/23.5

[56] References Cited

FOREIGN PATENT DOCUMENTS

WO 93/00103  7/1993  WIPO .

OTHER PUBLICATIONS

Coghlan, Focus, vol. 148, pp. 14–15, Nov. 25, 1995.
Brown, "News Media, Researchers 'Oversold' Gene Therapy, Advisory Panel Says", The Washington Post, Dec. 8, 1995.
Orkin et al., Report and Recommendations of the Panel to Assess the NIH Investment in Research on Gene Therapy, Dec. 7, 1995.
Hunter et al., "Retrovirus envelope glycoproteins" *Current Topics in Microbiology and Immunology* (1990) 157:187–253.
Ausbel et al., eds., "Transduction of genes using retrovirus vectors" *Current Protocols in Molecular Biology* (1992) John Wiley & Sons's, New York, Section III, pp. 9.10.1–9.14.3.
Vile et al., "A murine cell line producing HTLV–1 pseudotype virions carrying a selectable marker gene" *Virology* (1991) 180:420–424.
Miller et al., "Construction and properties of retrovirus packaging cells based on gibbon ape leukemia virus" *J. Virol.* (1991) 65(5):2220–2224.
Landau et al., "Pseudotyping with human T-cell leukemia virus type I broadens the human immunodeficiency virus host range" *J. Virol.* (1991) 65(1):162–169.

Emi et al., "Pseudotype formation of murine leukemia virus with the G protein of vesicular stomatitis viris" *J. Virol.* (1991) 65(3):1202–1207.
Dong et al., "A chimeric avian retrovirus containing the influenza virus hemagglutinin gene has an expanded host range" *J. Virol.* (1992) 66(12):7374–7382.
Kim et al., "Transport of cationic amino acids by the mouse ecotropic retrovirus receptor" *Nature* (1991) 352:725–728.
Johann et al., "GLVR1, a receptor for gibbon ape leukemia virus, is homologous to a phosphate permease of *Neurospora crassa* and is expressed at high levels in the brain and thymus" *J. Virol.* (1992) 66(3):1635–1640.
Ban et al., "Isolation and characterization of a 2.3-kilobase-pair cDNA fragment encoding the binding domain of the bovine leukemia virus cell receptor" *J. Virol.* (1993) 67(2):1050–1057.
Russell et al., "Retroviral vectors displaying functional antibody fragments" *Nucl. Acids Res.* (1993) 21(5):1081–1085.
Roux et al., "A versatile and potentially general approach to the targeting of specific cell types by retroviruses: application to the infection of Human cell by means of major histocompatibility complex class I and class II antigens by mouse ecotropic murine leukemia virus–derived viruses" *Proc. Natl. Acad. Sci. USA* (1989) 86:9079–9083.
Etienne–Julan et al., "the efficiency of cell targeting by recombinant retroviruses depends on the nature of the receptor and the composition of the artificial cell" *J. Gen. Virol.* (1992) 73:3251–3255.
Arai et al., "Cytokines: coordinators of immune and inflammatory responses" *Annu. Rev. Biochem.* (1990) 59:783–836.
Battini et al., "Receptor choice determinants in the envelope glycoproteins of amphotropic, xenotropic, and polytropic murine leukemia viruses" *J. Virol.* (1992) 66(3):1468–1475.
Gillis et al., "T cell growth factor: parameters of production and a quantitative microassay for activity" *J. Immunol.* (1978) 120 (6):2027–2032.
Goud et al., "Antibody–mediated binding of a murine ecotropic moloney retroviral vector to human cells allows internalization but not the establishment of the proviral state" *Virology* (1988) 163:251–254.

(List continued on next page.)

*Primary Examiner*—Jasemine C. Chambers
*Assistant Examiner*—Jill D. Schmuck
*Attorney, Agent, or Firm*—Morrison & Foerster

[57] ABSTRACT

The invention provides retroviral vectors which can be used for directing gene delivery to a specific sub-population of mammalian cells. The vectors comprise chimeric targeting proteins which specifically alter the host range of the vector. The chimeric targeting proteins contain a ligand moiety which is capable of binding to receptors present on target cells, and an uptake moiety which is capable of promoting entry of the vector into the target cell. The ligand moiety is derived from a cytokine that acts upon the target cells of interest, and the uptake moiety is derived from a retroviral envelope protein.

27 Claims, 5 Drawing Sheets

OTHER PUBLICATIONS

Hatakeyama et al., "Interleukin-2 receptor β chain gene: generation of three receptor forms by cloneduman α and β chain cDNA'" *Science* (1989) 244:551-71.556.

Linial et al., "Retroviral RNA packaging: sequence requirements and implications" *Current Topics in Microbiology and Immunology* (1990) 157:125-152.

Lupton et al., "Dominant positive and negative selection using a hygromycin phosphotransferase-thymidine kinase fusion gene" *Mol. Cell. Biol.* (1991) 11(6):3374-3378.

Matthews et al., "A receptor tyrosine kinase specific to hematopoietic stem and progenitor cell-enriched populations" *Cell* (1991) 65:1143-1152.

Miller et al., "Two base changes restore infectivity to a noninfectious molecular clone of moloney murine leukemia virus (pMLV-1) *J. Virol.* (1984) 49(1):214-222.

Miyajima et al., "Cytokine receptors and signal transduction" *Annu. Rev. Immunol.* (1992) 10:295-331.

Moore et al., "The clinical use of colony stimulating factors"*Annu. Rev. Immunol.* (1991) 9:159-191.

Nolta et al., "Retroviral vector-mediated gene transfer into primitive human hematopoietic progenitor cells: effects of mast cell growth factor (MGF) combined with other cytokines" *Exp. Hematol.* (1992) 20:1065-1071.

Oppenheim et al., "Properties of the novel proinflammatory supergene 'intercrine' cytokine family" *Annu. Rev. Immunol.* (1991) 9:617-648.

Takeshita et al., "Cloning of the γ chain of the human IL-2 receptor" *Science* (1992) 257:379-382.

Taniguchi et al., "Structure and expression of a cloned cDNA for human interleukin-2" *Nature* (1983) 302:305-310.

Waldmann, "The multi-subunit interleukin-2 receptor" *Annu. Rev. Biochem.* (1989) 58:875-911.

STRUCTURE OF MCS-LXSN-IL2ECO-env

ENVELOPE FUSION VECTORS FOR USE IN GENE DELIVERY

CROSS-REFERENCE TO RELATED APPLICATIONS

The application is the national phase of PCT Application No. PCT/US94/06128, filed Jun. 1, 1994; which is a continuation-in-part of U.S. patent application Ser. No. 08/070,117, filed Jun. 1, 1993 (now abandoned).

TECHNICAL FIELD

The present invention relates to retroviral vectors useful for introducing polynucleotides into target cells and more specifically to retroviral particles having on their surface chimeric targeting proteins capable of both binding to specific target cells via cellular cytokine receptors and mediating vector entry into the targeted cells.

BACKGROUND OF THE INVENTION

Retroviruses are a family of RNA viruses that contain RNA-directed DNA polymerase activity. These viruses possess similar structural characteristics, being membranous, icosahedral particles that are 70–120 nM in diameter and contain RNA as well as the structural and catalytic proteins necessary for infection of a host cell and subsequent reverse transcription of the viral genome. Retroviruses that are secreted from cells can be categorized into B-, C-, and D-type, lentiviruses, spumaviruses, and others, based on criteria relating to the shape of the nucleocapsid core within the particle, the nature of the budding process and the complexity of the viral genome, see, e.g., Weiss, R., et al., (1984 and 1985) "RNA Tumor Viruses," Cold Spring Harbor, N.Y.

Retroviruses typically have three common open reading frames, gag, pol and env, which encode the structural proteins, enzymatic activities including reverse transcriptase, and envelope proteins, respectively. The product of the env gene is a polyprotein precursor (typically referred to herein as the "envelope protein" or the "env protein"), that is proteolytically cleaved during transport to yield two polypeptides: a glycosylated protein found on the external surface of the particle (the "SU" protein), and a membrane-spanning or transmembrane protein (the "TM" protein); see, e.g., Hunter, E. and R. Swanstrom, Curr. Topics Microbiol. Immunol. 157:187–253, 1990. The SU protein is involved in recognizing and binding to cellular receptors, while the TM protein is involved in mediating the fusion of viral and cellular membranes necessary for viral uptake, id.

A retroviral vector is an infectious viral particle useful in achieving stable and efficient transduction of a gene into mammalian cells, including some cells that are not readily transfectable by other methods, such as primary cells of various types and also cells in vivo. Retroviral vectors based on murine C-type retroviruses have been used successfully for a number of years to introduce and express genes in cultured mammalian cells. Typically, retroviral vectors are produced by "packaging cell lines" that provide the necessary retroviral gag, pol and env gene products in trans, see, e.g., Miller et al., Human Gene Therapy 1:5–14 (1990); and Ausubel, F. M. et al. (eds), Units 9.10–9.14 in "Current Protocols in Molecular Biology," John Wiley & Sons, New York, 1992. This approach results in the production of retroviral particles which are highly infectious for mammalian cells, but are incapable of further replication after they have integrated into the genome of the target cell. Gene therapy protocols using retroviral vectors generally rely on a cell line containing the gag and pol genes, along with the env genes from an "amphotropic" (i.e. broad host range) virus such as 4070A amphotropic virus, which yields amphotropic progeny virus (e.g., the "PA317" cell line described by Miller and Buttimore, Mol. Cell. Biol. 6:2895, 1986).

Gene therapy protocols typically are ex vivo in nature, in that they require harvesting cells from the patient, culturing them in vitro, transducing them with the retroviral vector and returning the transduced cells to the patient; see, e.g., Kasid et al., Proc. Natl. Acad. Sci. USA 87:473, 1990; and Rosenberg et al., N. Engl. J. Med. 323:570, 1990.

In many situations, it would be desirable to restrict viral infection to a specific sub-population of the exposed cells. In such circumstances, the broad host range typical of retroviruses presents a substantial problem. Even where it is possible to purify the desired target cells, either before or after transduction, this necessitates undesirable manipulations of the cells and may be problematic in situations in which the preferred target cells are either difficult to purify or present at low or variable frequencies in mixed populations. Accordingly, it would be especially advantageous to have retroviral vectors which could specifically target particular sub-populations of mammalian cells.

A key determinant of viral host range is the "envelope" or "env" protein (encoded by the env gene) which is involved in binding to receptors on the surface of susceptible cells. The involvement of the env proteins, and the functional similarity among env proteins of various viruses, is illustrated by the well-documented phenomenon of "pseudotyping," in which the core proteins and nucleic acid are provided by one virus and the envelope proteins are provided by a different virus. A number of such pseudotyping experiments have demonstrated that the envelope proteins are largely responsible for the viral host-range. Functional pseudotypes have been demonstrated with the core proteins contributed by Moloney murine leukemia virus (Mo-MuLV) and the envelope proteins contributed by human T-cell leukemia virus (Vile et al., Virology 180:420, 1991), or Gibbon ape leukemia virus (Miller et al, J. Virol. 65:2220, 1991). Human T-cell leukemia virus has also been shown to pseudotype human immunodeficiency virus (Landau et al., J. Virol. 65:162, 1991). In addition, infectious virions have been produced when retrovirus cores have been pseudotyped by non-retroviral envelope proteins such as the G protein of vesicular stomatitis virus (Emi et al., J. Virol. 65:1207, 1991), or the hemagglutinin of influenza virus (Dong et al., J. Virol. 66:7374, 1992). These latter examples indicate that there are commonalities between various enveloped viruses and their mode of entry into cells.

Most retroviral envelope proteins appear to be capable of binding to a wide variety of cell types. As noted above, the retrovirus envelope protein used most commonly in gene therapy applications is that derived from 4070A amphotropic virus, which can bind to receptors present in numerous mammalian species, including humans, and on a wide variety of cell types within such species. Murine "ecotropic" viruses are relatively restricted in terms of susceptible host species (mouse and rat cells, not human cells, see, e.g., Delarco and Todaro, Cell 8:365–371, 1976); but even these utilize a receptor protein which is widely distributed in its expression within such species (Albritton et al., Cell 57:659, 1989). In fact, the receptor appears to be an amino acid transporter protein, serving a function critical for host cell viability (Kim et at., Nature 352:725, 1991). Similarly, the receptor for Gibbon Ape Leukemia Virus (O'Hara et al., Cell Growth Differ. 1:119, 1990), which also has sequences resembling those of a transporter, is expressed most abundantly in brain and thymus, but is also expressed at some level in all tissues and cells examined (Johann, et al., J. Virol. 66:1635, 1992). The bovine leukemia virus also utilizes a receptor which allows the virus to infect a wide variety of cell types (Ban et al., J. Virol. 67:1050, 1993). The best characterized example of a retrovirus-receptor interaction is in the human immunodeficiency virus (HIV) system. The primary receptor for HIV appears to be the CD4 molecule. (Maddon et al., Cell 47:333, 1986), which is expressed mainly on T-helper cells. However, HIV can also infect neuronal and other lymphoid cells through a CD4-mediated mechanism (Jordon et al., J. Virol. 65:736, 1991). Thus, a retroviral envelope protein having strict specificity for a particular cell type has not been characterized or identified.

There have been several attempts to confer specificity to retroviral infection. Russell et al. linked a single-chain antibody molecule to a retroviral envelope protein (Nucleic Acids Res 5:1081, 1993). The resulting protein was able to promote binding of viral particles to plastic dishes coated with the appropriate antibody; but binding to cells was not tested. It was unclear, therefore, whether such complexes could effectively bind to cells and, even if they could bind, whether they could also mediate viral uptake. Goud et al. attempted to link ecotropic Moloney murine leukemia virus (MoMLV) to human cells using an anti-(env) antibody and an anti-(human transferrin receptor) antibody (Virology 163:251, 1988). The two antibodies were linked by a third antibody directed against an immunoglobulin light chain determinant. Although it appeared that some internalization of the complex occurred using this "bridging" approach, there was no active infection. In another approach using antibody derivatives, Roux et al. linked an anti-(env) antibody to an antibody (W6/32) directed against an HLA framework epitope (PNAS 86:9079, 1989). In this study, some infection of human HeLa cells by the conjugates was achieved. Although such conjugates were also shown to work for targeting through a cytokine receptor, namely the EGF receptor, this approach did not appear to be generally applicable since a number of antibody conjugates did not work at all and, in those which exhibited some infectivity, the efficiency of targeting was reported to be quite low (Etienne-Julan et al., J. Gen. Virol., 73:3251-55, 1992). Neda et al. reported some infectivity of human hepatic cells, apparently via the galactose receptor, using viral particles with lactose on their surface (J. Biol. Chem. 266:14143-14146, 1991). Another indirect "bridging" approach attempted to exploit the known ability of lectins to bind glycoproteins by providing a variety of multivalent lectins which might bind, and therefore bridge, glycoconjugates on the cellular surface and those on the retroviral surface (Etienne-Julan, id.). Although binding was apparently detected, there was no observable infection of the target cells using such complexes.

SUMMARY OF THE INVENTION

In view of the continuing and unmet need for targeted retroviral vectors, the present invention provides a generalized approach for the construction of vectors which are capable of specifically targeting particular sub-populations of mammalian cells. In one aspect of the invention, targeting of the specific cells is also coupled to simultaneous cytokine stimulation of the targeted cells.

Thus, the invention provides chimeric targeting proteins, and polynucleotide constructs encoding such proteins, that specifically alter the host range of retroviral vectors, thereby enabling the directed targeting of mammalian cells. The chimeric targeting proteins, also referred to herein as "CTPs," contain a ligand moiety which is capable of binding to receptors present on the target cells, and an uptake moiety which is capable of promoting entry of the vector into the target cell. The ligand moiety is derived from a cytokine that acts upon the target cells of interest, and the uptake moiety is derived from a viral envelope protein or an analogous protein capable of promoting viral entry. In order to promote entry, the uptake moiety must as an initial matter allow display of the CTP on the viral surface. Subsequent penetration of the virus into the target cell can be mediated directly (i.e. with the uptake moiety of the CTP itself mediating membrane penetration) and/or indirectly (i.e. with the CTP functioning in combination with a co-expressed viral env protein displayed on the same viral surface). By incorporating the chimeric targeting proteins into the surface of a retroviral vector particle, the particle can be directed to a specific subset of cells bearing receptors for the ligand moiety. Additionally, in one aspect of the invention, the ligand moiety also acts as a functional cytokine, thereby simultaneously modulating the growth, differentiation or other cellular activity of the targeted cells.

Accordingly, one embodiment of the invention is a chimeric targeting protein (or "CTP") comprised of a ligand moiety and an uptake moiety, wherein the ligand moiety is an analog of a cytokine and is capable of binding to a cognate cytokine receptor present on the surface of a target cell, and wherein the uptake moiety is an analog of a viral envelope protein and is capable of promoting entry of the vector into the target cell. In a first type of CTP, the ligand moiety also exhibits "cytokine effector activity" (as defined herein), which can be used to modulate the growth, differentiation or other activity of the targeted cell. In a second type of CTP, the ligand moiety does not exhibit cytokine effector activity. In a preferred embodiment, the uptake moiety has a reduced ability (i.e. a completely or partially reduced ability) to bind to the natural env receptors but retains the ability to promote viral uptake. In another preferred embodiment, the ligand moiety and the uptake moiety are separated by a flexible peptide linker sequence, or "flexon," which is believed to enhance the ability of the moieties to adopt conformations relatively independently of each other.

Another embodiment of the invention is a polynucleotide encoding a CTP, and plasmids comprising such a polynucleotide, which can be used to transform retroviral packaging cells thereby enabling the production of retroviral vectors bearing chimeric targeting proteins on their surfaces.

Another embodiment of the invention is a retroviral packaging cell line producing retroviral vectors bearing chimeric targeting proteins on their surfaces.

Yet another embodiment of the invention is a retroviral particle bearing on its surface a CTP comprised of a ligand moiety and an uptake moiety, wherein the ligand moiety is an analog of a cytokine and is capable of binding to a cognate cytokine receptor present on the surface of a target cell, and wherein the uptake moiety is an analog of a viral envelope protein and is capable of promoting entry of the vector into the target cell.

Still another embodiment of the invention is a method of using a retroviral particle, bearing on its surface a CTP, for targeting a mammalian cell, wherein the targeting results in the uptake and incorporation of vector nucleic acid by the targeted cell, which method can be used to introduce a heterologous gene into the targeted cell.

Still another embodiment of the invention is a cell produced by the above-described method, and progeny thereof.

DETAILED DESCRIPTION OF THE INVENTION

Figure 1:
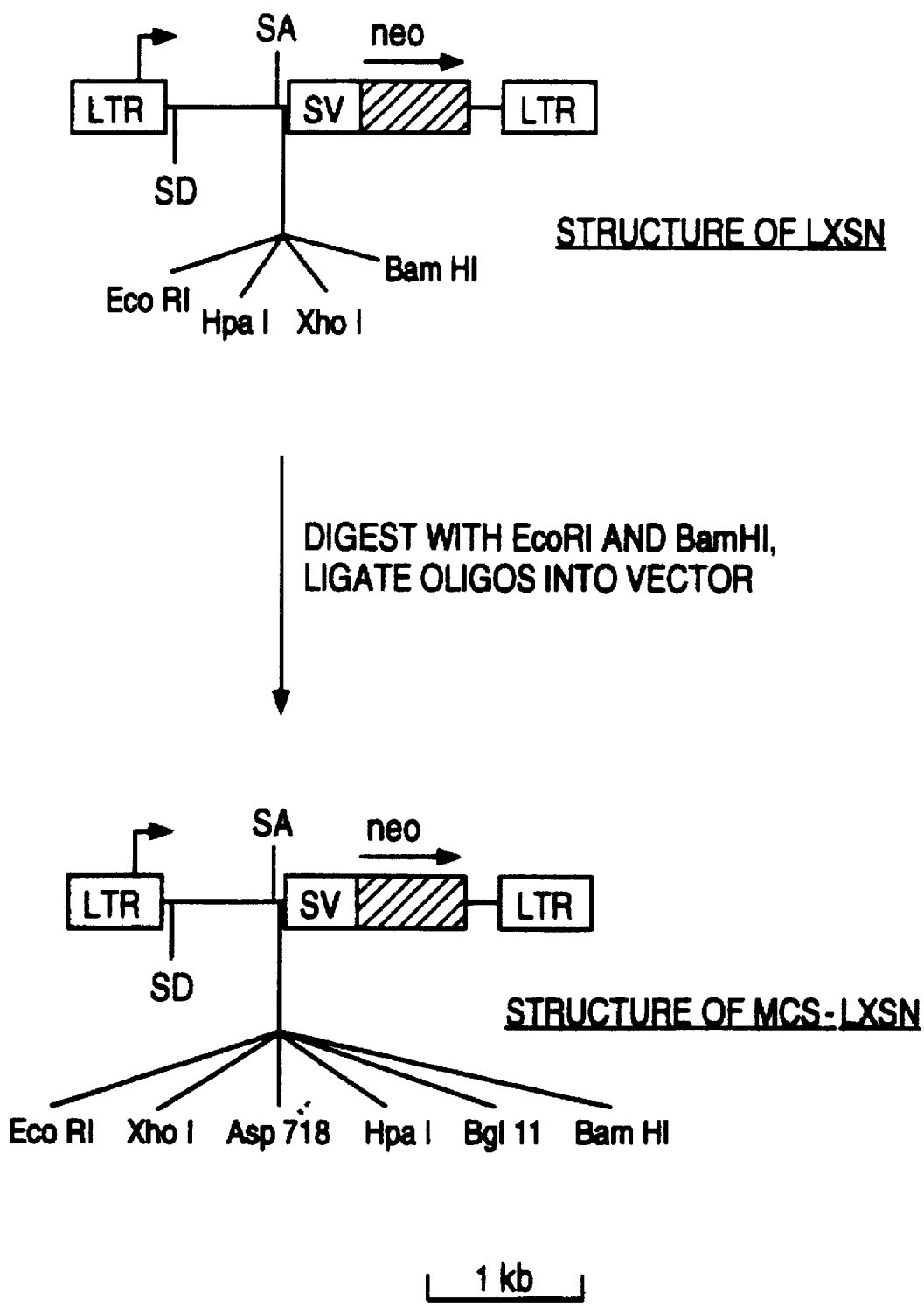
FIG. 1 is a schematic diagram showing the construction of the MCS-LXSN vector.
Figure 2:
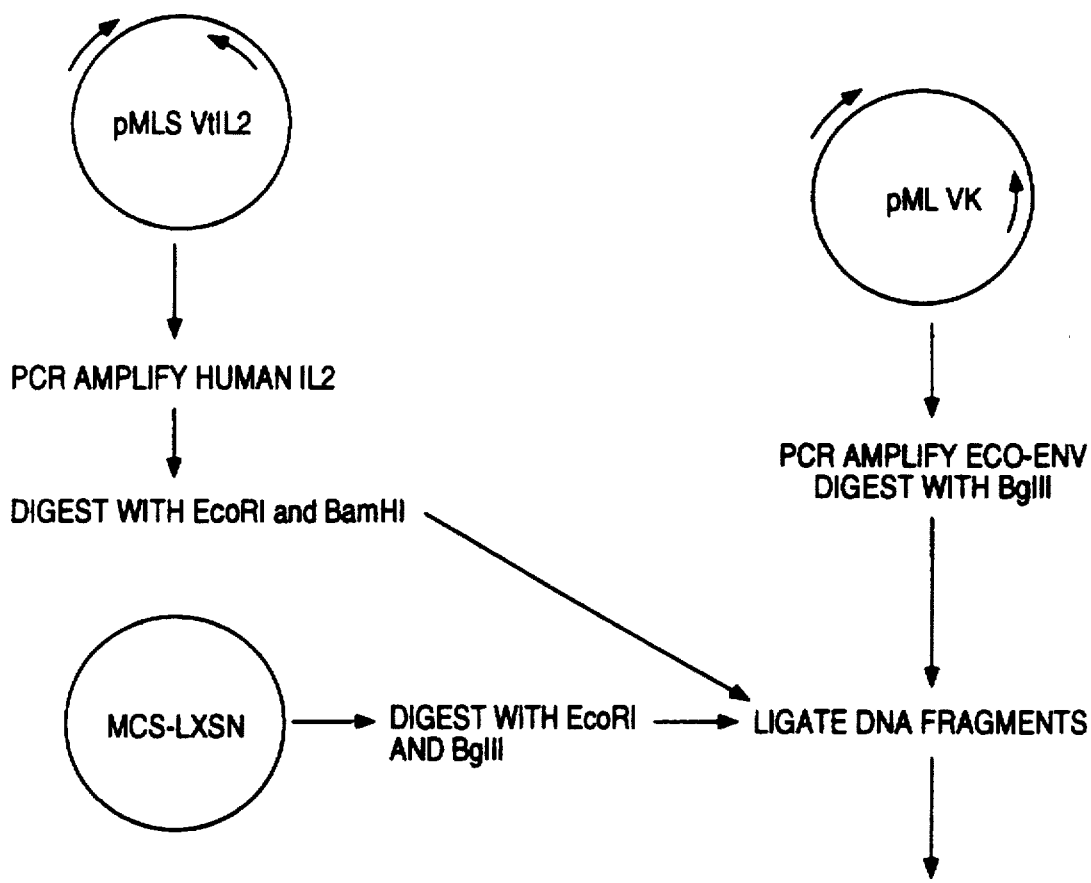
FIG. 2 is a schematic diagram showing the construction of the MCS-LXSN-IL2eco-env retroviral vector, where the sequence encoding the CTP (the IL2eco-env sequence) was inserted between the EcoRI and BglII sites of the MCS-LXSN vector.
Figure 2:
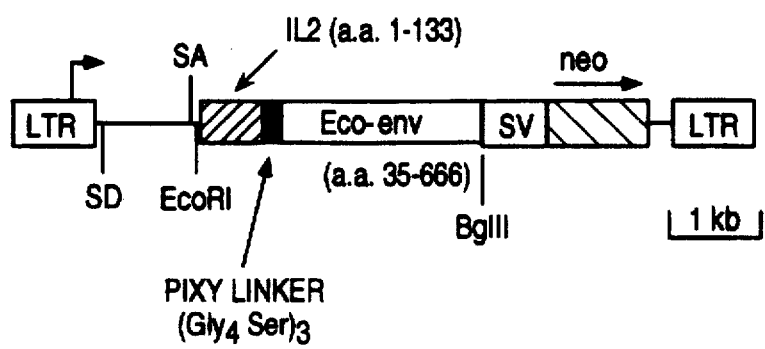

In accordance with the present invention, novel retroviral targeting vectors are prepared having chimeric targeting proteins, or "CTPs," on their outer surface. Each CTP is itself comprised of a ligand moiety which is capable of binding to cytokine receptors present on the surface of a target cell, and an uptake moiety which is capable of promoting virus entry into the target cell. The CTPs of the present invention allow for the construction of retroviral vectors which can be used to target a specific sub-population of cells (i.e. those bearing cognate receptors for the CTP). Retroviral targeting vectors constructed with a first type of CTP also exhibit cytokine effector activity, which can be used to simultaneously modulate the growth, differentiation or other activity of the targeted cell. Targeting vectors constructed with a second type of CTP do not exhibit such cytokine effector activity.

In a preferred embodiment, the uptake moiety has a reduced ability (i.e. a completely or partially reduced ability) to bind to the natural env receptors but retains the ability to promote viral uptake.

In another preferred embodiment, the ligand moiety and the uptake moiety are separated by a flexible peptide linker sequence, or "flexon," which is believed to enhance the ability of the moieties to adopt conformations relatively independently of each other.

In another preferred embodiment of the present invention, a DNA sequence encoding the cytokine interleukin-2, or IL-2, is fused in-frame with a sequence encoding the envelope protein of the ecotropic Moloney murine leukemia virus (MoMLV), or the amphotropic murine virus 4070A, such that the fusion protein generated comprises a signal peptide for insertion through the plasma membrane, the complete sequence corresponding to the native IL-2 protein, and the complete sequence encoding the mature env protein from MoMLV or the 4070A virus. In the resulting CTP, both the IL-2 domain (constituting the ligand moiety), and the env domain (constituting the uptake moiety), are functional in biological assays for IL-2 activity and virus entry, respectively. The CTP is then expressed in a packaging cell line, such as LGPS, to produce a virus particle that is capable of (i) binding to cell surface receptors on target cells; (ii) causing cytokine effector activity in the target cells; and (iii) mediating uptake of the vector RNA by the target cells.

In other embodiments of the present invention, any cytokine cDNA sequence encoding a polypeptide capable of binding to a cell surface cytokine receptor is fused to any sequence encoding a molecule capable of promoting virus entry, which latter sequences may be obtained from viruses including other retroviruses (see, e.g., Hunter, E. and R. Swanstrom, Curr. Topics Microbiol. Immunol. 157:187–253, and other references cited herein); vesicular stomatitis virus (see, e.g., Rose and Gallione J. Virol. 39:519–528); influenza virus (see, e.g., Gething and Sambrook, Nature (London) 300:598–603, 1981); and paramyxoviruses (see, e.g., Morrison and Portner p. 347–382 in D. W. Kingsbury (ed.), "The Paramyxoviruses," Plenum Press, New York.

The terms "polypeptide" and "protein" are used interchangeably to refer to polymers of amino acids and do not refer to any particular lengths of the polymers. These terms also include post-translationally modified proteins, for example, glycosylated, acetylated, phosphorylated proteins and the like. Also included within the definition are, for example, proteins containing one or more analogs of an amino acid (including, for example, unnatural amino acids, etc.), proteins with substituted linkages, as well as other modifications known in the art, both naturally occurring and non-naturally occurring.

"Native" proteins or polynucleotides refer to proteins or polynucleotides recovered from a source occurring in nature, and fragments thereof. Thus, the phrase "native envelope proteins" would refer to naturally occurring envelope proteins, and fragments thereof.

"Mutein" forms of a protein or polypeptide are those which have minor alterations in amino acid sequence caused, for example, by site-specific mutagenesis or other manipulations; by errors in transcription or translation; or which are prepared synthetically. Minor alterations are those which result in amino acid sequences wherein the biological activity of the polypeptide is retained and/or wherein the mutein polypeptide has at least 90% homology with the native form.

The term "polynucleotide" as used herein refers to a polymeric form of nucleotides of any length, either ribonucleotides or deoxyribonucleotides. This term refers only to the primary structure of the molecule. Thus, double—and single-stranded DNA, as well as double—and single stranded RNA are included. It also includes modified polynucleotides such as methylated or capped polynucleotides.

A "replicon" refers to a polynucleotide comprising an origin of replication, an ori sequence, which allows for replication of the polynucleotide in an appropriate host cell. Examples include chromosomes and plasmids.

An "open reading frame" (or "ORF") is a region of a polynucleotide sequence which can encode a polypeptide; the region may represent a portion of a protein coding sequence or an entire coding sequence.

A "transcriptional regulatory region" or "transcriptional control region" refers to a polynucleotide encompassing all of the cis-acting sequences necessary for transcription, and may include sequences necessary for regulation. Thus, a transcriptional regulatory region includes at least a promoter sequence, and may also include other regulatory sequences such as enhancers, and transcription factor binding sites.

"Operably linked" refers to a juxtaposition wherein the components so described are in a relationship permitting them to function in their intended manner. For instance, a promoter sequence is operably linked to a coding sequence if the promoter sequence promotes transcription of the ceding sequence.

"Transformation," as used herein, refers to the insertion of an exogenous polynucleotide into a host cell, irrespective of the method used for the insertion, which methods include, for example, viral infection, transfection, electroporation and direct uptake. The exogenous polynucleotide may be maintained as an extrachromosomal replicon such as a plasmid, or alternatively, may be integrated into the host cell genome.

"Recombinant," as applied to a polynucleotide, means that the polynucleotide is the product of various combinations of cloning, restriction and/or ligation steps resulting in a construct having a sequence distinguishable from homologous sequences found in nature. "Recombinant" may also be used to refer to the protein product of a recombinant polynucleotide. Typically, DNA sequences encoding the structural coding sequence for, e.g., cytokines, can be assembled from cDNA fragments and short oligonucleotide linkers, or from a series of oligonucleotides, to provide a synthetic gene which is capable of being expressed when operably linked to a transcriptional regulatory region. Such sequences are preferably provided in the form of an open reading frame uninterrupted by internal nontranslated sequences (i.e. "introns"), such as those commonly found in eukaryotic genes.

The term "recombinant expression vector" refers to a replicon which is capable of being introduced into a target cell (by, e.g., viral infection, transfection, electroporation or direct uptake), and which contains a transcriptional regulatory region and coding sequences necessary for the expression of a recombinant protein.

"Recombinant host cells", "host cells", "cells", "cell lines", "cell cultures", and other such terms denoting microorganisms or higher eukaryotic cells refer to cells which can be, or have been, used as recipients for recombinant vectors or other transfer polynucleotides, and include the progeny of the original cell which has been transformed. It is understood that the progeny of a single cell may not necessarily be completely identical (in morphology or in genomic or total DNA complement) to the original parent cell, due to natural, accidental, or deliberate mutation.

"Blood cell" refers to cells found either circulating in the blood, in tissue, or in bone marrow, and includes cells of the myelocytic series, the monocytic series, the megakaryocytic series, the erythrocytic series, the lymphocytic series, and the plasmocytic series. The characterization of such cells is described in "The Morphology of the Blood Cells" (1985).

"Lymphohematopoietic progenitor cells" are cells which are typically obtained from the bone marrow or peripheral blood and which are capable of giving rise, through cell division, to any mature cells of the lymphoid or hematopoietic systems. This term includes committed progenitor cells with significant though limited capacity for self-renewal, as well as the more primitive cells capable of forming spleen colonies in a CFU-S assay, and still more primitive cells possessing long-term, multilineage re-populating ability in a transplanted mammalian host.

"Lymphocytes" as used herein, are spherical cells with a large round nucleus (which may be indented) and scanty cytoplasm. They are cells that specifically recognize and respond to non-self antigens, and are responsible for development of specific immunity. Included within "lymphocytes" are B-lymphocytes and T-lymphocytes of various classes.

A "primary culture of cells" or "primary cells" refer to cells which have been derived directly from in vivo tissue and not passaged. Primary cultures can be distinguished from cell strains and established cultures principally by the retention of a karyotype which is substantially identical to the karyotype found in the tissue from which the culture was derived, and by the cellular responses to manipulations of the environment which are substantially similar to the in vivo cellular responses.

"Retroviruses" are a class of viruses which replicate using RNA-directed DNA polymerase, or reverse transcriptase, to replicate a viral RNA genome to provide a double-stranded DNA intermediate which is incorporated into chromosomal DNA of an avian or mammalian host cell. A characteristic feature of retroviral genomes is the retroviral long terminal repeat ("LTR") which is an untranslated region found in slightly variant forms at both the 5' and 3' ends of the retroviral genome. The retroviral LTR includes a tRNA primer binding site, and signals for initiation of transcription by RNA polymerase II and 3' cleavage and polyadenylation of RNA transcripts. The 5' LTR also contains a transcriptional promoter which is generally active in mammalian cells. Most retroviral vectors are derived from murine retroviruses. Retroviruses adaptable for use in accordance with the present invention can, however, be derived from any vertebrate cell source. Many such retroviruses are known to those skilled in the an and are described, for example, in Weiss et al., eds, *RNA Tumor Viruses*, 2d ed., Cold Spring Harbor, N.Y. (1984 and 1985). Plasmids containing retroviral genomes are also widely available, from the American Type Culture Collection (ATCC) and other sources. The nucleic acid sequences of a large number of these viruses are known and are generally available, for example, from databases such as GENBANK.

A "provirus" refers to the DNA reverse transcript of a retroviral vector RNA which is stably integrated into chromosomal DNA in a suitable host cell, or a cloned copy thereof.

A "retroviral particle" or a "retroviral vector" as used herein refers to an infectious retroviral particle comprising RNA having cis-acting packaging sequences (i.e. "vector RNA" as defined herein), proteins encoded by the gag and pol genes, and outer surface proteins involved in binding to and entry of mammalian cells. The outer surface proteins may comprise either native retroviral envelope proteins (i.e. the gene products of a native retroviral env gene) or "chimeric targeting proteins," as defined herein.

A "retroviral targeting vector," is a retroviral vector in which the outer surface proteins are "chimeric targeting proteins," as defined herein.

A viral "envelope protein" or "env protein" refers to a protein found on the outer surface of a viral particle that is involved in mediating binding and uptake of the virus into a host cell. The envelope proteins of retroviruses are typically encoded by the env gene. The native retroviral env gene product is generally a polyprotein precursor that is proteolytically cleaved during transport to yield two polypeptides: an external, glycosylated polypeptide (the "SU" protein) and a membrane-spanning or transmembrane protein (the "TM" protein); see, e.g., Hunter, E. and R. Swanstrom, Curt. Topics Microbiol. Immunol.

157:187–253, 1990. The SU protein is involved in recognizing and binding to cellular receptors and the TM protein is involved in mediating the fusion of viral and cellular membranes necessary for viral uptake, id.

An "analog of a viral envelope protein," which forms the uptake moiety of the present invention, refers to an amino acid sequence which comprises at least that portion of a viral envelope protein (or an analogous protein) that is required for anchoring the protein to the viral surface and/or mediating uptake of the virus into a host cell, or a mutein of such a portion of an envelope protein or analogous protein. An analog of an envelope protein may, but need not, contain the portion of an envelope protein that is involved in binding of the viral particle to a receptor on a target cell.

"Trans-acting sequences" refer to sequences which need not be present on the same replicon as a second sequence in order to affect the expression, activity or some other characteristic of the second sequence. Examples of such trans-acting sequences in the context of retroviral vectors include the products of the gag, pol, and env genes (structural proteins, reverse transcriptase and other enzymes, and envelope proteins, respectively).

"Cis-acting sequences" refer to sequences which must be closely linked a second sequence in order to affect the expression, activity or some other characteristic of the second sequence. Examples of such cis-acting sequences in the context of retroviral vectors include the promoters, reverse transcription signals, integration sequences and packaging sequences which are generally present in the retroviral genome (or retroviral "vector RNA," as defined herein).

"Packaging sequences" refer to cis-acting nucleic acid sequences which are typically present in retroviral genomic RNA and which allow the genomic RNA to be recognized by the proteins involved in encapsidation and, therefore, allow the RNA to be packaged within retroviral particles.

"Vector RNA" refers to any RNA sequence comprising a packaging sequence which allows the RNA to be encapsidated into retroviral vectors when the gene products of the gag, pol and env genes are present in a cell. After contacting the resulting vector with a susceptible target cell, the vector RNA can be taken up by the target cell, reverse transcribed, and incorporated into the target cell genome.

"Cytokine," as used herein, refers to a polypeptide that is an intercellular signalling molecule. A number of such molecules have been identified and characterized, including for example: interleukins (such as IL-1α, IL-1β, IL-2, IL-3, IL-4, IL-5, IL-6, IL-7, IL-9 (P40), IL-10, IL-11, IL-12 and IL-13); CSF-type cytokines such as GM-CSF, G-CSF, M-CSF, LIF, EPO, TNF-α and TNF-β); interferons (such as IFN-α, IFN-β, IFN-γ); cytokines of the TGF-β family (such as TGF-β1, TGF-β2, TGF-β3, inhibin A, inhibin B, activin A, activin B); chemotactic factors (such as NAP-1, MCP-1, MIP-1α, MIP-1β, MIP-2, SISβ, SISδ, SISε, PF4, PBP, γIP-10, MGSA); growth factors (such as EGF, TGF-α, aFGF, bFGF, KGF, PDGF-A, PDGF-B, PD-ECGF, INS, IGF-I, IGF-II, NGF-β); α-type intercrine cytokines (such as IL-8, GRO/MGSA, PF4, PBP/CTAP/βTG, IP-10, MIP-2, KC, 9E3); and β-type intercrine cytokines (such as MCAF, ACT-2/PAT 744/G26, LD-78/ PAT 464, RANTES, G26, I309, JE, TCA3, MIP-1α,β, CRG-2). A number of other cytokines are also known to those of skill in the art. The sources, characteristics, targets and effector activities of these cytokines have been described and, for many of the cytokines, the DNA sequences encoding the molecules are also known; see, e.g., Van Snick, J. et al. (1989) J. Exp. Med.
169:363–368; Paul, S. R. et al. (1990) Proc. Natl. Acad. Sci. USA 87:7512–7516; Gately, M. K. et al. (1991) J. Immunol. 147:874–882; Minty, A., et al. (1993) Nature 362:248; and the reviews by Arai, K., et al. (1990) Annu. Rev. Biochem. 59:783–836; Oppenheim, J. J., et al. (1991) Annu. Rev. Immunol. 9:617–48; Waldman, T. A. (1989) Annu. Rev. Biochem. 58:875–911; Beutler, B., et al. (1988) Annu. Rev. Biochem. 57:505–18; Taniguchi, T. (1988) Annu. Rev. Immunol. 6:439–64; Paul, W. E. et al., (1987) Annu. Rev. Immunol. 5:429–59; Pestka, S. et al., (1987) Annu. Rev. Biochem. 56:727–77; Nicola, N. A. et al. (1989) Annu. Rev. Biochem. 58:45–77; Miyajima, A., et al. (1992) Ann. Rev Immunol. 10:295–331; and Schrader, J. W. (1986) Annu. Rev. Immunol. 4:205–30; and the particular references reviewed and/or cited therein, which are hereby incorporated by reference in their entirety. Also included in the definition of a cytokine is the cytokine that interacts with the flk-2 receptor on totipotent hematopoietic stem cells, see, e.g. Matthews, W. et al., Cell 65:1143–1152, 1991.

An "analog of a cytokine," which forms the ligand moiety of the present invention, refers to an amino acid sequence which contains at least that portion of a cytokine polypeptide which is required for binding to receptors for the cytokine on the surface of mammalian cells, or a mutein of such a portion of a cytokine polypeptide. An analog of a cytokine may, but need not, contain the portion of the cytokine which is involved in "cytokine effector activity," as defined herein.

"Cytokine effector activity" refers to the modulation of growth, differentiation or other cellular response to a cytokine.

A "cognate" receptor of a given ligand refers to the receptor normally capable of binding such a ligand.

A "ligand moiety" refers to an analog of a cytokine which is capable of binding to a cognate cytokine receptor present on the surface of a mammalian cell. The ligand moiety is typically encoded by a sequence which is derived from a nucleic acid sequence encoding a native cytokine or a mutein thereof.

An "uptake moiety" refers to an analog of a viral envelope ("env") protein or an analogous protein that is capable of promoting entry into a target cell. In order to promote entry, the uptake moiety must as an initial matter allow display of the CTP on the viral surface. Subsequent penetration of the virus into the target cell can be mediated directly (i.e. with the uptake moiety of the CTP itself mediating membrane penetration) and/or indirectly (i.e. with the CTP functioning in combination with a co-expressed viral env protein displayed on the same viral surface). In a preferred embodiment, the uptake moiety can directly mediate membrane penetration. The uptake moiety is typically encoded by a sequence which is derived from a nucleic acid sequence encoding a native viral envelope protein or a mutein thereof; or an analogous protein that is capable of anchoring the CTP to the viral surface and/or mediating membrane penetration.

A "chimeric targeting protein" or "CTP" refers to a protein comprising a ligand moiety and an uptake moiety, wherein the ligand moiety is an analog of a cytokine and is capable of binding to a cognate cytokine receptor present on the surface of a target cell, and wherein the uptake moiety is an analog of a viral envelope protein and is capable of promoting entry into a target cell, as described above. In a first type of CTP, the ligand moiety also exhibits cytokine effector activity which can be used to modulate the growth, differentiation or other activity of the targeted cell. In a second type of CTP, the ligand moiety does not exhibit cytokine effector activity. Since the chimeric targeting proteins possess an uptake moiety which can function in a manner analogous to that of native viral envelope proteins, retroviral vectors can be made in which the envelope proteins are replaced by CTPs, or by a combination of a CTP and a second (co-expressed) envelope protein. The CTPs of the present invention can, like native retroviral envelope proteins, be provided in trans. Thus, the sequence encoding the CTP can be stably integrated into the genome of the packaging cell line or may be present on an extrachromosomal replicon such as a plasmid. Since the proteins can be provided in trans, the RNA transcript encoding the CTP need not (but may) form part of the vector RNA which will be incorporated into the retroviral targeting vector. Including the sequence encoding the CTP on the vector RNA will generally result in the CTP sequence being delivered and, if operably linked to a suitable promoter, expressed in the target cells. Where such expression is not desirable, it will be preferable to separate the sequence encoding the CTP from the vector RNA. By using a packaging cell line with the sequence encoding the CTP stably incorporated, it will be possible to prepare retroviral targeting vectors containing a variety of different vector RNAs, simply by introducing a plasmid or other vector encoding the desired vector RNA into the packaging cell line.

A "flexon" refers to a flexible polypeptide linker sequence (or to a nucleic acid sequence encoding such a polypeptide) which typically comprises amino acids having small side chains. In the present invention, flexons are preferably incorporated in the CTP between the ligand moiety and the uptake moiety. Incorporating flexons between those moieties is believed to promote functionality of both the ligand moiety and the uptake moiety by allowing each moiety to adopt a conformation relatively independently from the other moiety. Most of the amino acids incorporated into the flexon will preferably be amino acids having small side chains such as glycine, alanine, valine, leucine, isoleucine and serine. The flexon will preferably comprise between about four and one hundred amino acids, more preferably between about eight and fifty amino acids, and most preferably between about ten and thirty amino acids. "Pixy" sequences, as described in U.S. Pat. No. 5,073,627 and 5,108,910, will also be suitable for use as flexons.

"Packaging cell lines" are mammalian cell lines which provide the necessary retroviral gag, pol and, in some cases, env gene products in trans. Thus, in a packaging cell line, vector RNA lacking, for example, the gag and pol sequences, can nevertheless be encapsidated into retroviral particles which are highly infectious for mammalian cells, but are incapable of further replication after they have integrated into the genome of the target cell. Cell lines containing packaging genes (particularly an env gene) derived from an "amphotropic" (i.e. broad host range) retrovirus provide amphotropic progeny virus (e.g., the cell line "PA317," ATCC CRL 9078, described by Miller and Buttimore, Mol. Cell. Biol. 6:2895, 1986). The product of the env gene is responsible for the binding of the native retroviruses to receptors on the surface of the target cell and is, therefore, a critical determinant of the host range of the retrovirus. The PA317 cells produce retroviral particles with an amphotropic envelope protein, which can transduce cells of human and other mammalian species origin. Other packaging cell lines produce particles with "ecotropic" (i.e. narrow host range) envelope proteins, which are only able to transduce mouse and rat cells. For example, the ψ2 packaging cell line (described by Mann, R. et al., Cell 33:153–159, 1983), contains a Moloney ecotropic helper provirus from which the "packaging sequences" have been deleted (so that transcripts encoding the trans-acting factors are not themselves packaged). The "LGPS" cell line (Miller et al., J. Virol. 65:2220, 1991), does not express any envelope protein, but does express all of the other trans-acting proteins required for encapsidation. Thus, the chimeric targeting proteins of the present invention, expressed in a cell such as LGPS, would yield retroviral targeting vectors bearing the CTPs on their surfaces in place of any native retroviral envelope proteins.

The practice of the present invention will employ, unless otherwise indicated, a number of conventional techniques of molecular biology, microbiology, recombinant DNA, and immunology, which are within the skill of the art. Such techniques are explained fully in the literature, see, e.g., Sambrook, Fritsch, and Maniatis, "Molecular Cloning: A Laboratory Manual," Second Edition (1989); F. M. Ausubel et al. (eds.), "Current Protocols in Molecular Biology," (1987 and 1992); M. J. Gait (ed.), "Oligonucleotide Synthesis," (1984); R. I. Freshney (ed.), "Animal Cell Culture," (1987); J. M. Miller and M. P. Calos (eds.), "Gene Transfer Vectors for Mammalian Cells," (1987); M. Kriegler, "Gene Transfer and Expression: A Laboratory Manual," (1991); D. M. Weir and C. C. Blackwell (eds.), "Handbook of Experimental Immunology;" J. E. Coligan, A. M. Kruisbeek, D. H. Margulies, E. M. Shevach and W. Strober, (eds.), "Current Protocols in Immunology," (1991); and the series entitled "Methods in Enzymology," (Academic Press, Inc.). All patents, patent applications, and publications mentioned herein, both supra and infra, are hereby incorporated herein by reference.

Construction of Recombinant Expression Vectors Encoding Chimeric Targeting Proteins The chimeric targeting proteins of the present invention are comprised of a region encoding a ligand moiety and a region encoding an uptake moiety, wherein the ligand moiety is an analog of a cytokine and is capable of binding to a cognate cytokine receptor present on the surface of a target cell, and wherein the uptake moiety is an analog of a viral envelope protein and is capable of promoting entry of the vector into the target cell.

The ligand moiety of the CTPs will be an analog of a cytokine. Cytokines are intercellular signalling molecules involved in the regulation of mammalian somatic cells. Several families of cytokines, both growth promoting and growth inhibitory in their effects, have been characterized. An analog of a cytokine, which forms the ligand moiety of the present invention, refers to an amino acid sequence which contains at least that portion of a cytokine polypeptide which is required for binding to receptors for the cytokine on the surface of mammalian cells, or a mutein of such a portion of a cytokine polypeptide. An analog of a cytokine may, but need not, contain the portion of the cytokine which is involved in "cytokine effector activity," as defined herein. Cytokines for use in the present invention include, for example, interleukins (such as IL-1α, IL-1β, IL-2, IL-3, IL-4, IL-5, IL-6, IL-7, Il-9 (P40), Il-10, Il-11, Il-12 and Il-13); CSF-type cytokines such as GM-CSF, G-CSF, M-CSF, LIF, EPO, TNF-α and TNF-β); interferons (such as IFN-α, IFN-β, IFN-γ); cytokines of the TGF-β family (such as TGF-β1, TGF-β2, TGF-β3, inhibin A, inhibin B, activin A, activin B); chemotactic factors (such as NAP-1, MCP-1, MIP-1α, MIP-1β, MIP-2, SISβ, SISδ, SISε, PF-4, PBP, γIP-10, MGSA); growth factors (such as EGF, TGF-α, aFGF, bFGF, KGF, PDGF-A, PDGF-B, PD-ECGF, INS, IGF-I, IGF-II, NGF-β); α-type intercrine cytokines (such as IL-8, GRO/MGSA, PF-4, PBP/CTAP/βTG, IP-10, MIP-2, KC, 9E3); and β-type intercrine cytokines (such as MCAF, ACT-2/PAT 744/G26, LD-78/PAT 464, RANTES, G26, 1309, JE, TCA3, MIP-1α,β, CRG-2). A number of other cytokines are also known to those of skill in the art. The sources, characteristics, targets and effector activities of these cytokines have been described and, for many of the cytokines, the DNA sequences encoding the molecules are also known; see, e.g., Van Snick, J. et al. (1989) J. Exp. Med. 169:363–368; Paul, S. R. et al. (1990) Proc. Natl. Acad. Sci. USA 87:7512–7516; Gately, M. K. et al. (1991) J. Immunol. 147:874–882; Minty, A., et al. (1993) Nature 362:248; and the reviews by Arai, K., et al. (1990) Annu. Rev. Biochem. 59:783–836; and Oppenheim, J. J., et al. (1991) Annu. Rev. Immunol. 9:617–48; Waldman, T. A. (1989) Annu. Rev. Biochem. 58:875–911; Beutler, B., et al. (1988) Annu. Rev. Biochem. 57:505–18; Taniguchi, T. (1988) Annu. Rev. Immunol. 6:439–64; Paul, W. E. et al., (1987) Annu. Rev. Immunol. 5:429–59; Pestka, S. et al., (1987) Annu. Rev. Biochem. 56:727–77; Nicola, N. A. et al. (1989) Annu. Rev. Biochem. 58:45–77; and Schrader, J. W. (1986) Annu. Rev. Immunol. 4:205–30; and the particular references reviewed and/or cited therein, which are hereby incorporated by reference in their entirety. Many of the DNA sequences encoding cytokines are also generally available from sequence databases such as GENBANK. Typically, cloned DNA encoding such cytokines will already be available as plasmids—although it is also possible to synthesize polynucleotides encoding the cytokines based upon the published sequence information. Polynucleotides encoding the cytokines can also be obtained using polymerase chain reaction (PCR) methodology, as described, for example, by Mullis and Faloona (1987) Meth. Enzymology 155:335. The detection, purification, and characterization of cytokines, including assays for identifying new cytokines effective upon a given target cell type, have also been described in a number of publications, including, e.g., Clemens, M. J. et al. (eds.) (1987) "Lymphokines and Interferons," IRL Press, Oxford; and DeMaeyer, E., et al. (1988) "Interferons and Other Regulatory Cytokines," John Wiley & Sons, New York; as well as the references referred to above.

The cytokines suitable for targeting a particular subpopulation of cells will be those which bind to receptors present on cells of that sub-population. As new cytokines are characterized, these can be employed in the present invention as long as they exhibit the desired binding characteristics and specificity. The identification and characterization of cytokines, and the use of assays to test the ability of cytokines to activate particular target cells, are known in the art; see, e.g., Clemens, M. J. et al. (eds.) (1987) "Lymphokines and Interferons," IRL Press, Oxford; and DeMaeyer, E., et al. (1988) "Interferons and Other Regulatory Cytokines," John Wiley & Sons, New York; as well as the references referred to above.

The target cells for a large number of cytokines are already known, as noted above; and, in many cases, the particular cell surface receptors for the cytokine have already been identified and characterized; see, e.g., the references referred to above. Typically, the cell surface receptors for cytokines are transmembrane glycoproteins that consist of either a single chain polypeptide or multiple protein subunits. The receptors bind their cognate ligands with high affinity and specificity, and may be widely distributed on a variety of somatic cells, or quite specific to given cell subsets. The presence of cytokine receptors on a given cell type can also be predicted from the ability of a cytokine to modulate the growth or other characteristics of the given cell; and can be determined, for example, by monitoring the binding of a labeled cytokine to such cells; and other techniques, as described in the references cited above.

A large number of cytokine receptors have been characterized and many of these are known to belong to receptor families which share similar structural motifs; see, e.g., the review by Miyajima, A., et al., Ann. Rev. Immunol. 10:295–331 (1992), and the publications reviewed therein, hereby incorporated by reference. Type-I cytokine receptors (or hematopoietic growth factor receptors) include, for example, the receptors for IL-2, IL-3, IL-4, IL-5, IL-6, IL-7, GM-CSF, G-CSF, EPO, CNTF and LIF. Type-II cytokine receptors include, for example, the receptors for IFN-α, IFN-β and IFN-γ. Type-III cytokine receptors include, for example, the receptors for TNF-α, TNF-β, FAS, CD40 and NGF. Type-IV cytokine receptors (immunoglobulin-like, or "Ig-like," receptors) include the receptors for IL-1; and the receptors for IL-6 and G-CSF (which have Ig-like motifs in addition to the Type-I motif). These receptor families are described for example, in Smith et al., Science 248:1019–1023, 1990); Larsen et al., J. Exp. Med., 172:1559–1570, 1990); McMahan et al., EMBO J. 10:2821–2832, 1991); and in the reviews by Cosman et al., Trends Biochem Sci 15:265–269, 1990); and Miyajima, A., et al., Ann. Rev. Immunol. 10:295–331 (1992), and the publications reviewed therein, all of which are hereby incorporated by reference.

The role of particular cytokines in the regulation of various cellular systems is well known in the art. In the hematopoietic system, for example, the hematopoietic colony-stimulating factors and interleukins regulate the production and function of mature blood-forming cells. Lymphocytes are dependent upon a number of cytokines for proliferation. For example, CTLs are dependent on helper T ($T_H$) cell-derived cytokines, such as IL-2, IL4 and IL-7, for growth and proliferation in response to foreign antigens. (Zinkernagel and Doherty, Adv. Immunol. 27:51, 1979; Male et al., Advanced Immunology, Chap. 7, Cower Publ., London, 1987; Jacobson et al., J. Immunol. 133:754, 1984). IL-2, for example, is a potent mitogen for cytotoxic T lymphocytes (Gillis and Smith, Nature 268:154, 1977), and the combination of antigen and IL-2 cause proliferation of primary $CD4^+$ T cells in vitro. The importance of IL-2 for the growth and maintenance of the $CD8^+$ CTL in vivo has been documented in models of adoptive immunotherapy in which the therapeutic efficacy of transferred anti-retroviral $CD8^+$ cells is enhanced on subsequent administration of IL-2 (Cheever et al., J. Exp. Med. 155:968, 1982; Reddehase et al., J. Virol. 61:3102, 1987). IL-4 and IL-7 are also capable of stimulating the proliferation of mature $CD8^+$ CTL (Alderson et at., J. Exp. Med. 172:577, 1990).

Cytokines may be either secreted from the cells that synthesize them, such as IL-2, −3, −4, −5, −6, −7, or they may be membrane-bound, such as MGF and CSF-1 (thus permitting stimulation of the target cell only when in contact with the producer cell). In the case of IL-2, the IL-2 receptors are expressed on T-cells, B-cells, natural killer cells, glioma cells and cells of the monocyte lineage (Smith, Science 240:1169, 1988). However, the greatest level of high affinity IL2 receptor expression is observed in activated T-cells (Waldemann, Ann. Rev. Biochem. 58:875, 1989). The IL2 receptor complex consists of three protein components, a low affinity receptor, α, Tac or p55 (Leonard et al., Nature 311:626, 1984), an intermediate affinity receptor, β or p70 (Hatakeyama, Science 244:551, 1989), and a signal transduction protein, δ or p64, which itself does not bind IL2, but which interacts with the p70 receptor subunit (Takeshita et al., Science 257:379, 1992). The combination of the p55 and p70 subunits together make up the high affinity form of the IL2 receptor (Hatakeyama, Science 244:551, 1989), which is characteristically observed on activated T-cells. The cellular targets of a large number of the other cytokines are known and described in the reviews and other references cited above. Furthermore, following the approaches described in those references, any particular cell population or sub-population can be readily assayed for sensitivity to a given cytokine.

The CTPs of the present invention can be grouped into two different types based on the resulting cytokine effector activity of the ligand moiety. In chimeric proteins of the first type, the targeting protein will possess cytokine effector activity which can be used to modulate the targeted cells in accordance with the activity of the cognate cytokine. Typically, chimeric proteins of the first type will be prepared by incorporating the entire cytokine coding sequence into a polynucleotide encoding the CTP; although it will also be possible to remove portions of the cytokine sequence which are neither required for binding to the receptor nor essential for cytokine effector activity. In such cases, the CTPs will provide a combination of activities comprising: (i) binding to specific target cells; (ii) delivery of vector nucleic acid into the targeted cell; and (iii) cytokine modulation of the cells thus targeted. Such a combination of activities will allow, for example, the transformation of particular cells to be coupled to the proliferation of the transformed cells. This will be generally advantageous in the context of gene delivery since it can be used to promote the proliferation and thus the transformation of the targeted cells in a given cell population; and will be particularly advantageous for in vivo gene delivery where it may be otherwise problematic or impossible to induce the targeted cells to divide and thus promote stable incorporation of the transferred gene.

In some cases, it will be preferable to make use of the receptor binding potential of the cytokine domain without concomitant cytokine effector activity. This may be the case, for example, when a cytokine with suitable receptor binding properties has a negative or unwanted effect on target cell activity. Thus, in CTPs of the second type, the targeting protein will not possess significant cytokine effector activity and will not, therefore, cause cytokine modulation of the target cell population. Typically, CTPs of the second type will be prepared from cytokine sequences in which the domain responsible for effector activity has been mutationally altered by, e.g., substitution, insertion or deletion. For example, IL-2 has been subjected to deletion analysis to identify which portions of the sequence are involved in receptor binding and which are critical for cytokine effector activity; see, e.g., Brandhuber, B. J. et al., J. Biol. Chem. 262:12306–308, 1987; Brandhuber, B. J. et al., Science 238:1707–09, 1987; Zurawski, S. M. et al., EMBO J. 7:1061–69, 1988; and Arai, K., et al., Annu. Rev. Biochem. 59:783–836, 1990. The receptor binding and effector domains of a number of other cytokines have similarly been characterized; see Arai et al., id, and other reviews and references cited therein.

The rapidity with which novel cytokines and receptors have recently been molecularly cloned has generated a wide array of these molecules. In particular, the combination of direct cDNA expression cloning and screening assays for either induction of proliferation of binding to specific cell surface receptors on target cells has led to many new molecules being cloned (see, for example, Cosman et al., Trends Biochem Sci 15:265–269, 1990). The advent of these technologies will undoubtedly lead to the cloning of more cytokines which, on the basis of their binding characteristics and specificity may be used in the context of the present invention as the ligand moiety of the CTP. Ligand moieties derived from the flk-2 ligand will be of interest because the cytokine binds specifically to a receptor, flk-2, which appears to be expressed on early hematopoietic cells (Matthews, W. et al., Cell 65:1143, 1991). In the context of the present invention, CTPs comprising a ligand moiety derived from the flk-2 ligand could thus be used to direct infection to lymphohematopoietic progenitor cells.

The CTPs of the present invention also comprise an uptake moiety which is an analog of a viral envelope protein (or an analogous protein that is capable of promoting entry into a target cell). An analog of a viral envelope protein refers to an amino acid sequence which comprises at least that portion of a viral envelope protein (or an analogous protein) that is required for anchoring the protein to the viral surface and/or mediating membrane penetration of a target cell, or a mutein of such a portion of an envelope protein or analogous protein. An analog of an envelope protein may, but need not, contain the portion of an envelope protein that is involved in binding of the viral particle to a receptor on a target cell. A large number of retroviruses have been characterized and, for many of these, the nucleotide sequence of the viral genome has been published. As described herein, (see, e.g., the fourth paragraph under "Detailed Description of the Invention", supra, and the Examples below), a preferred viral envelope protein is derived from a retrovirus; more preferably a C-type retrovirus; and most preferably from murine C-type retroviruses such as Moloney murine leukemia virus or the amphotropic 4070A murine retrovirus. Typically, the retroviral genome comprises three open reading frames, gag, pol and env. The envelope proteins encoded by various retroviral env genes generally share functional homology, even though there may be considerable variation among the primary amino acid sequences. The native env gene product is typically a polyprotein precursor that is proteolytically cleaved during transport to the cell surface to yield two polypeptides: a glycosylated polypeptide on the external surface (the "SU" protein) and a membrane-spanning or transmembrane protein (the "TM" protein); see, e.g., Hunter, E. and R. Swanstrom, Curr. Topics Microbiol. Immunol. 157:187–253, 1990. Typically, the env proteins are found to associate into oligomeric structures and appear as "knob" like structures on the surface when viewed by electron microscopy, id. Examples of these pairs of SU and TM proteins and the viruses from which produce them are: gp52 and gp36 from mouse mammary tumor virus (Racevskis, J. et al., J. Virol. 35:937–48, 1980); gp85 and gp37 from Rous sarcoma virus (Hunter et al., J. Virol. 46:920, 1983); gp70 and p15E from Moloney murine leukemia virus (Koch et al., 49:828, 1984); gp70 and gp20 from Mason Pfizer monkey virus (Bradac, J. et al., Virology 150:491–502, 1986); gp120 and gp41 from human immunodeficiency virus (Kowalski, M. et al., Science 237:1351–1355, 1987); and gp46 and gp21 from human T-Cell leukemia virus (Seiki et al., Proc. Natl. Acad. Sci. 80:3618, 1983); and others described in the references cited herein. The surface, or SU, proteins are responsible for binding to specific receptors on the surface of target cells as a first step in the infection process. The transmembrane, or TM, proteins, as well as associating with viral core proteins through their C-terminal ends, are responsible for a critical membrane fusion event which takes place after binding and allows entry of the virus into the cell (Hunter and Swanstrom, Curr. Top. Micro. and Immunol. 157:187, 1990). This membrane fusion event is accomplished by a hydrophobic peptide sequence present at the amino terminus of the TM protein. This mechanism for viral entry, in which an oligomeric env protein complex binds to a specific cell surface receptor and subsequently mediates virus entry, frequently by means of a hydrophobic membrane-disruptive domain, is a common theme among enveloped viruses, including influenza virus and many such molecules are known to those skilled in the art, see, e.g., Hunter and Swanstrom, Curr. Top. Micro. and Immunol. 157:187, 1990. Examples of retroviruses which can be used in the present invention include murine retroviruses such as Harvey murine sarcoma virus (Ha-MSV), Kirsten murine sarcoma virus (Ki-MSV), Moloney murine sarcoma virus (Mo-MSV), various murine leukemia viruses (MuLV), mouse mammary tumor virus (MMTV), murine sarcoma virus (MSV) and rat sarcoma virus (RaSV); bovine leukemia virus (BLV); feline retroviruses such as feline leukemia virus (FeLV) and feline sarcoma virus (FeSV); primate retroviruses such as baboon endogenous virus (BaEV), human immunodeficiency viruses (HIV-I and HIV-II), human T-cell leukemia viruses (HTLV-I and HTLV-II), Gibbon ape leukemia virus, Mason Pfizer monkey virus (M-PMV), simian immunodeficiency virus (SIV) and simian sarcoma virus (SSV); various lentiviruses; and arian retroviruses such as arian erythroblastosis virus, arian leukosis virus (ALV), arian myeloblastosis virus, avian sarcoma virus (ASV), avian reticuloendotheliosis-associated virus (REV-A), Fujinami sarcoma virus (FuSV), spleen necrosis virus (SNV) and Rous sarcoma virus (RSV). Many other suitable retroviruses are known to those skilled in the art and a taxonomy of retroviruses is provided by Teich, pp. 1–16 in Weiss et al., eds, RNA Tumor Viruses, 2d ed., Vol. 2, Cold Spring Harbor, N.Y. Plasmids containing retroviral genomes are also widely available from the ATCC and other sources. The nucleic acid sequences of a large number of these viruses are known and are available, for example, from databases such as GENBANK.

The functional similarity among env proteins, and the ability to "swap" env proteins derived from different viruses, is further illustrated by the well-documented phenomenon of "pseudotyping," in which the core proteins and nucleic acid are provided by a first virus and the envelope proteins (determining host range) are provided by a different virus. Functional pseudotypes have been demonstrated with the core proteins contributed by Moloney murine leukemia virus (Mo-MuLV) and the envelope proteins contributed by human T-cell leukemia virus (HTLV) (Vile et al., Virology 180:420, 1991), Gibbon ape leukemia virus (Miller et al. J. Virol. 65:2220, 1991). Human T-cell leukemia virus has also been shown to pseudotype human immunodeficiency virus (Landau et al., J. Virol. 65:162, 1991). In addition, infectious virions have been produced when Moloney virus cores have been pseudotyped by non-retroviral envelope proteins such as the G protein of vesicular stomatitis virus (Emi et al., Virol. 65:1207, 1991), or the hemagglutinin of influenza virus (Dong et al., J. Virol. 66:7374, 1992). These latter examples indicate that there are functional commonalities between various enveloped viruses and their mode of entry into cells which will allow the use of envelope proteins from a variety of sources.

The sequences of a large number of such env proteins are known, and are generally available from sequence databases such as GENBANK. Furthermore, polynucleotides encoding env proteins can be readily obtained from retroviral particles themselves—which typically contain two strands of genomic RNA comprising the gag, pol and env genes. Such RNA molecules can be reverse transcribed with reverse transcriptase using well-known procedures. Also, since many different envelope genes have been cloned and characterized, plasmids containing DNA encoding envelope proteins are available from a number of different sources. Polynucleotides encoding the env gene products can also be obtained using polymerase chain reaction (PCR) methodology, as described, for example, by Mullis and Faloona (1987) Meth. Enzymology 155:335.

In one embodiment of the present invention, the uptake moiety is prepared from the entire coding region of a retroviral env gene, in which case the CTP can be used to target cells normally susceptible to the retrovirus from which the env gene was derived, as well as cells bearing receptors to the ligand moiety. In other embodiments of the present invention, the targeting is restricted to cells bearing receptors for the cytokine corresponding to the ligand moiety of the CTP. Where it is desirable to limit targeting to cells bearing the appropriate cytokine receptors, there are at least two approaches within the present invention which can be used to achieve such specificity. One approach is to utilize a ligand moiety which is based on a cytokine with a very high binding affinity for the desired target cells compared to the binding affinity of the uptake moiety of the CTP for native env protein receptors. Since many of the cytokines are known to exhibit very high affinity binding to their receptors, and since it will be possible to base the uptake moiety on a lower-binding-affinity envelope protein, targeting can be effectively focused upon those cells bearing the cognate cytokine receptor. Of course, as exemplified herein, targeting can also be limited to cells bearing the appropriate cytokine receptor by using an uptake moiety derived from a virus for which there are no functional receptors (or only poorly functioning receptors) on cells exposed to the virus bearing the CTP (e.g., using the uptake moiety from a murine "ecotropic" (i.e. narrow host range) virus on human cells). As noted above, murine ecotropic viruses are normally restricted in terms of susceptible host species to mouse and rat cells (and will not, therefore, normally bind to human cells); see the discussion of retroviral envelope proteins in the Background of the Invention, supra, and Battini et al., cited infra. Additionally, regions of envelope proteins can be exchanged resulting in the creation of mutant envelope proteins that retain functional integrity with respect to uptake, but have altered receptor specificity (see, e.g., Battini et al., id.). See also, the Examples below, illustrating the preparation of uptake moieties based on murine ecotropic env ("eco-env") constructs. Another suitable approach to limiting binding is to base the uptake moiety on a mutant envelope protein in which the mutation has disrupted the ability of the envelope protein to engage in binding via the native env protein receptor but has not interfered with the ability of the envelope protein to promote viral uptake. Plasmids encoding such mutant env proteins are available in the art; and it will also be well within the ability of one skilled in the an to prepare new versions of such env protein mutants. As discussed above, however, the mutations must not disrupt the ability of the envelope protein to promote viral uptake. Accordingly, these mutations can be prepared by, for example, deleting small segments of the coding region (or adding small segments to it), or by introducing non-conservative amino acid substitutions into the coding sequence. In contrast, deleting large segments of the envelope protein (or replacing large segments with, for example, the ligand moiety) is not preferred because large structural changes can interfere with or completely disrupt the ability of the envelope protein to be displayed on the viral surface and/or to mediate membrane penentration. As illustrated in the Examples below, preferred CTPs of the present invention can be conveniently prepared by fusing the ligand moiety, preferably via a flexon (which is believed to further promote the retention of functionality), to a complete or nearly complete envelope protein, preferably at or in close proximity to the amino terminus of the mature envelope protein in the examples illustrated below.

Typically, it will be preferable to prepare mutations in the amino-terminal region of the env protein since this region typically contains the domain involved in binding to the env receptor, see, e.g., Weiss, R. et al. in Weiss, R. et al. (eds.) RNA Tumor Viruses, Cold Spring Harbor, N.Y. (1984 and 1985). In the murine leukemia virus (MuLV) system, for example, it is well known that the amino-terminal region of the gp70 molecule is involved in binding to cell surface receptors, see, e.g., Heard and Danos, J. Virol. 65:4026–4032, 1991. Battini et al., J. Virol. 66:1468–1475 (1992) have also reported that portions of the amino-terminal region of gp70 can be exchanged in order to switch binding to different MuLV env receptors without interfering with the ability of the protein to interact with p15E TM protein (and, thereby, to mediate viral uptake). Similarly, in the human immunodeficiency virus (HIV) system, mutational analysis of gp120 has identified portions of the molecule which are critical for binding to the CD4 receptor, see, e.g., Kowalski, M. et al., Science 237:1351–1355, 1987. Yet another approach to identify the region critical for receptor binding is as follows: an antibody known to inhibit binding can be used to immuno-affinity purify a cleavage fragment of the env protein; which fragment is then partially sequenced to identify the corresponding domain of the env protein to be deleted or otherwise mutagenized, see, e.g., Laskey, L. A. et al., Cell 50:975–985, 1987. Such techniques can be employed in the present invention to generate CTPs in which the uptake moiety remains capable of promoting viral entry, but the specificity of binding is principally determined by the presence of cognate cytokine receptors rather than env protein receptors.

The term "recombinant expression vector" refers to a replicable DNA sequence used to express a gene which encodes a protein (such as the CTPs of the present invention) and which includes a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Generally, DNA sequences encoding the CTPs disclosed herein can be assembled from cDNA fragments to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Of course, sequences of non-translated DNA may be present 5' or 3' the open reading frame where such sequences do not interfere with manipulation or expression of the coding regions.

The CTPs of the present invention, like native viral envelope proteins, can be provided in trans. Thus, the sequence encoding the CTP can be stably integrated into the genome of a packaging cell line or may be present on an extrachromosomal element such as a plasmid or other vector. Since the proteins can be provided in trans, the RNA transcript encoding the CTP need not be part of the vector RNA which will be incorporated into the retroviral targeting vector. Including the sequence encoding the CTP on the vector RNA will generally result in the CTP being delivered, and potentially expressed, in the target cells. Where such expression is not desirable, it will be preferable to separate the sequence encoding the CTP from the vector RNA. By using a packaging cell line with the sequence encoding the CTP stably incorporated, it will be possible to prepare retroviral targeting vectors containing a variety of different vector RNAs, simply by introducing into the cell a plasmid or other vector encoding the particular vector RNA.

The CTPs of the present invention are preferably prepared as a fusion protein in which the ligand moiety and the uptake moiety are expressed as a single polypeptide. Thus, the sequence encoding the cytokine domain will preferably be linked to the sequence encoding the envelope domain such that an in-frame translational fusion of the two regions results, allowing the CTP to be translated from a single open reading frame. However, as discussed herein, CTPs can also be co-expressed on the surface of viral particles with a separate protein that further promotes viral entry. For example, a CTP can be co-expressed (on the surface of the same viral particle) with a separate viral envelope protein or analog thereof. Such a strategy can be used to enhance the infectivity of the virus bearing the CTP. Similarly, the ability to express cytokine molecules on the surface of the viral particle, as described in the Examples below, illustrates that env-cytokine chimeras are transported to the cell surface and displayed on the viral surface. The uptake moiety of the CTP (whether derived from an envelope protein or an analogous protein that is capable of anchoring proteins in membranes) can thus simply mediate display of the CTP on the surface of the viral particle. Such a CTP can then be co-expressed on the viral particle with a second protein (such as a functional envelope protein) to mediate penetration of the virus into the target cell. This strategy can thus be used to target infection to specific cells, or to enhance infection frequencies for specific target cels.

In preparing the fusion proteins of the present invention, it is preferable that moieties such as the ligand moiety and the uptake moiety are separated by flexible polypeptide linker sequences, referred to as "flexon" sequences. Incorporating flexons between the different moieties of the present invention is believed to promote functionality of both the ligand and the uptake moiety by allowing a moiety on one side of the flexon to adopt a conformation relatively independently from that of the moiety on the other side of the flexon. The majority of the amino acids making up the flexon will preferably be amino acids having small side chains such as glycine, alanine, valine, leucine, isoleucine and serine. The flexon will preferably comprise between about four and one hundred amino acids, more preferably between about six and forty amino acids, and most preferably between about ten and thirty amino acids. "Pixy" sequences, as described in U.S. Pat. No. 5,073,627 and 5,108,910, will also be suitable for use as flexons. See, also, Huston et al. Proc. Natl. Acad. Sci. USA 85:5879–5883 (1988); Colcher et al. J. NCI 82, #14 (1990); and Bedzyk et al., J. Biol. Chem. 265, 18615–18620 (1990).

The CTPs of the present invention may be readily constructed from cDNAs encoding the desired segments, although other methods will be apparent to those of ordinary skill in the art. In one method, for example, the DNA encoding the CTP is prepared by providing cloned cDNAs encoding a cytokine and a viral envelope protein.

The cloning of such sequences can be accomplished using well-known techniques of DNA manipulation as described, for example, in Sambrook, Fritsch, and Maniatis, MOLECULAR CLONING: A LABORATORY MANUAL, Second Edition, 1989; and F. M. Ausubel et al., eds., CURRENT PROTOCOLS IN MOLECULAR BIOLOGY, John Wiley & Sons, New York, 1992. In some cases, cloned cDNAs prepared by restriction enzyme digestion may contain unwanted sequences that would intervene in the fusion or cause a shift of the reading frame. The unwanted sequences can be removed by techniques known to those of ordinary skill in the art, including loop-out site-directed mutagenesis or splice-overlap extension polymerase chain reaction (PCR). For convenience, there are also a variety of commercially available linkers which can be used to join the two fragments in any of the three potential reading frames. The sequence of the chimeric cDNA encoding the targeting protein can be confirmed by standard DNA sequencing methods.

A polynucleotide region encoding the CTP will generally be operably linked to transcriptional control regions that allow expression of the CTP. Control regions include, at least a promoter and a ribosomal binding site, and may also include, inter alia, enhancer regions, splice regions, polyadenylation regions, transcription and/or translation termination regions, and transcription and/or translation factor binding sites. As is well known in the art, there are a number of such control sequences which can be used to provide various levels of expression, which may be either constitutive or regulatable in a variety of ways. These control regions may be present in recombinant vectors, particularly in recombinant expression vectors. Transcription of the CTP can be conveniently driven from the same retroviral promoter which generally drives transcription of the envelope gene, i.e. the retroviral LTR promoter. There are also a large number of other promoters known to be effective for use in mammalian cells and which can be used in place of the LTR promoter. It will also be advantageous to include a Kozak consensus sequence upstream of the initiator methionine for the open reading frame (Kozak et al., Nucl. Acid. Res. 15:3374, 1987). A large number of such transcriptional control regions are known in the art and, for many of these, their relative strength of promoting transcription in various types of cells has been characterized. In the present invention, the CTP must be expressed before assembly of the retroviral targeting vectors can occur and therefore the promoter driving transcription of the CTP coding sequence should be active in the packaging cell line. In some cases, as discussed below, it will be preferable that the CTP not be actively expressed in a target cell. In such cases, the CTP coding sequence can be placed downstream of a promoter which is active in the packaging line but not active in the target cells or the CTP coding sequence can be segregated from the vector RNA and expressed from another locus in the packaging line (e.g. by integrating the CTP coding sequence into the packaging cell genome or into an extrachromosomal replicon in the packaging cell).

Preferably, the polynucleotide construct encoding the CTP will contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; Co) complement auxotrophic deficiencies, or (c) supply critical nutrients not available from complex media. The choice of the proper selectable marker will depend on the host cell, and appropriate selectable markers for different hosts are well known in the art. If the construct will also be incorporated into the vector RNA (and, thus, the retroviral vector), then the selectable marker can also be used to monitor uptake of the vector by the target cell, and incorporation of the provirus in the target cell. A commonly used selectable marker is the n gene which provides a selectable marker both during cloning steps in bacteria (neomycin resistance) and in mammalian cells (G418 resistance). The neo gene is preferably under the control of a promoter which is active in mammalian cells, such as the SV40 early region promoter. A large variety of other selectable markers and promoters, which are well known in the art, can also be used with the present invention.

Techniques for nucleic acid manipulation are described generally, for example, in Sambrook et al. (1989), supra., Ausubel et al. (1987), supra. and in Annual Reviews of Biochemistry (1992) 61:131–156. Reagents useful in applying such techniques, such as restriction enzymes and the like, are widely known in the art and commercially available from a number of vendors.

Large amounts of the polynucleotides used to create the CTP of the present invention may be produced by replication in a suitable host cell. The natural or synthetic polynucleotide fragments coding for a desired fragment may be incorporated into recombinant expression vectors. Purification of nucleic acids produced by the methods of the present invention can be achieved by methods known in the art and described, e.g., in Sambrook et al. (1989), supra; and Ausubel et al. (1992), supra.

The polynucleotides used in the present invention may also be produced in part or in total by chemical synthesis, e.g., by the phosphoramidite method described by Beaucage and Carruthers, Tetra. Letts. 22:1859–1862, 1981; or the triester method according to Matteucci et al., J. Am. Chem. Soc. 103:3185, 1981; and may be performed on commercial automated oligonucleotide synthesizers. A double-stranded fragment may be obtained from the single stranded product of chemical synthesis either by synthesizing the complementary strand and annealing the strand together under appropriate conditions or by enzymatically synthesizing the complementary strand using DNA polymerase with an appropriate primer sequence.

Production of Retroviral Targeting Vectors

Typically, the retroviral vectors will be produced in retroviral packaging cells which have been made to express all of the required trans-acting factors required for the production of retroviral particles, but which are unable to generate particles with any genome unless specific vectors are introduced which have the correct cis-acting sequences (including packaging sequences) to allow for packaging of transcripts. Trans-acting factors include the proteins (normally encoded by the viral genome) which are required for encapsidation of the viral genome, entry of virions into the target cells and reverse transcription of the viral genome. A number of suitable packaging lines have been described and are widely available, see, e.g., Ausubel et al. (1992), supra. Cis-acting elements are sequences which are introduced into the RNA to be packaged (i.e. the vector RNA) to allow for the production of viral particles containing the vector RNA. The retroviral particles produced by such a packaging line will, therefore, contain the vector RNA of interest and will be infectious on mammalian cells by virtue of the CTP on their surface; but they will be unable to mediate ongoing rounds of infection in targeted cells since the transduced polynucleotide will not encode all of the trans-acting factors necessary for viral production.

Expression of the viral envelope protein is required for the viral binding and entry step. To independently examine the contribution of different envelope proteins, and also to make infection dependent upon the CTP, it is preferable to use a cell line such as LGPS (Miller et al., J. Virol. 65:2220, 1991), which does not express a retroviral env protein but does express all of the other necessary trans-acting proteins. Thus, in LGPS cells, the surface of the retroviral particle will comprise CTPs without any native env proteins. As discussed above, the sequence encoding the CTP can be stably integrated into the genome of the packaging cell line or may be present on an extrachromosomal element such as a plasmid or other vector. Since the proteins can be provided in trans, the RNA transcript encoding the CTP need not be pan of the vector RNA which will be incorporated into the retroviral targeting vector. Including the sequence encoding the CTP on the vector RNA will generally result in the CTP being delivered, and potentially expressed, in the target cells. Where such expression is not desirable, it will be preferable to separate the sequence encoding the CTP from the vector RNA. By using a packaging cell line in which the sequence encoding the CTP has been incorporated, it will be possible to prepare a new retroviral targeting vector (comprising a new vector RNAs), simply by introducing a nucleic acid sequence encoding the desired vector RNA into the packaging cells. Stable integration of a gene encoding the CTP can be achieved by using a retroviral or other vector to introduce the CTP coding sequence into a packaging line, such as LGPS; following methods such as those applied to the numerous packaging lines already known in the art; see, e.g., Miller et al., Human Gene Therapy 1:5–14, 1990; and the general references cited above. Viral infection or transfection of packaging cells, and the selection of infected or transfected cells, will be performed according to widely used techniques, such as those described by Sambrook et al. (1989), supra; and Ausubel et al. (1992), supra. The production of retroviral particles from the packaging cell lines and characterization of the particles is described, for example, Sambrook et al. (1989), supra; and Ausubel et al. (1992), supra.

There are a number of publications describing the construction and use of retroviral vectors including, for example, Weiss, R., et al., (1985) "RNA Tumor Viruses, Cold Spring Harbor, N.Y. Preferably, the vector RNA construct (which will be delivered to the target cells) will contain a positive selectable marker—a gene encoding a protein necessary for the survival or growth of a host cell transformed with the vector RNA. The presence of this gene ensures the growth of only those targeted cells which stably express the transduced nucleic acid. Typical positive selectable markers encode proteins that (a) confer resistance to antibiotics or other toxic substances, e.g. neomycin, methotrexate, etc.; (b) complement auxotrophic deficiencies, or (c) supply critical nutrients not available from complex media. The choice of the proper selectable marker will depend on the host cell, and appropriate markers for different hosts are well known in the art. The selectable marker can also be used to monitor the incorporation of the vector into a transfected cell and can also be used to monitor uptake of the vector by the target cell, and incorporation of the provirus in the target cell. A commonly used selectable marker is the neo gene which provides a selectable marker both during cloning steps in bacteria (neomycin resistance) and in mammalian cells (G418 resistance).

In the retroviral vector, the neo gene is preferably under the control of a promoter which is active in mammalian cells, such as the neo early region promoter. Any other genes that are to be delivered for expression in the target cells can be operably linked to a promoter which is known to be active or activatable in the target cell of interest. A large number of promoters are well known in the art, including, for example, regions isolated from the following: the human cytomegalovirus (HCMV) IE94 promoter region (M. Boshart et al. (1985), Cell 41:521–530); the human IL-2 gene (T. Fujita et al. (1986), Cell 46:401–407); the human IFN-γ gene (V. C. Ciccarone et al. (1990), J. Imunol. 144:725–730); the human IL-3 gene (S. G. Shoemaker et al. (1990), Proc. Natl. Acad. Sci. USA 87:9650–9654); the human IL-4 gene (N. Arai et al. (1989), I. Immunol. 142:274–282); the human lymphotoxin gene (G. E. Nedwin et al., S. L. Naylor, A. Y. Sakaguchi, D. Smith, J. Jarrett-Nedwin, D. Pennica, D. V. Goeddel, and P. W. Gray, (1985); Human lymphotoxin and tumor necrosis factor genes (Nucl. Acids. Res. 13:6361–6373); the human granulocyte-macrophage CSF (GM-CSF) gene (S. Miyatake et al. (1985), EMBO J. 4:2561–2568; the human perforin gene (M. G. Lictenheld et al. (1989), J. Immunol. 143:4267–4274); the human 519 gene (W. C. Manning et al. (1992), J. Immunol. 148:4036–4042); the human granzyme B (CTLA-1) gene (P. Haddad et al. (1990), Gene 87:265–271; the human CTLA-4 gene (K. Harper et al. (1991), J. Immunol. 147:1397–1044); the human CGL-2 gene (J. W. Heusel et al. (1991), J. Biol. Chem. 266:6152–6158); the human granzyme H gene (P. Haddad et al. (1990), Int. Immunol. 3:57–66; the human IL-2 receptor, α chain gene (S. L. Cross et al. (1987), Cell 49:47–56); the murine T cell activation 3 (TCA-3) gene (S. D. Wilson et al. (1988), J. Immunol 141:1563–1570); and the human CD69 gene.

Of particular use for targeting lymphocytes are transcriptional control regions that are responsive to lymphocyte activation and which, therefore, coordinate expression with antigenic activation of the lymphocyte, as described in U.S. Ser. No. 08/044,539, filed 06 Apr., 1993. Transcriptional control regions that are predominantly active in activated CD4$^+$ helper T cells (T$_H$ cells) include those from the IL-2 and IL-4 genes. Those predominantly active in activated CD8$^+$ CTLs include those from the following genes: lymphotoxin, perforin, 519, Granzyme H, CTLA-1, and CGL-2. Of particular interest are those active in both activated CD4$^+$ T$_H$-cells and CD8$^+$ CTLs, including inter alia, transcriptional control regions from the following genes: IFN-γ, IL-3, GM-CSF, CTLA-4, the IL-2 receptor α chain, TCA-3, and CD69.

It is also contemplated that overexpression or continued expression of a gene or genes introduced into a targeted cell may be toxic, or otherwise undesirable, to an individual human or other mammal harboring such targeted cells. Therefore, it is within the scope of the invention to include gene segments that cause the targeted cells of the invention to be susceptible to negative selection in vivo. By "negative selection" is meant that the targeted cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia, the following: the Herpes simplex virus type I thymidine kinase (HSV-I TK) gene (Wigler et al., Cell 11:223, 1977), which confers ganciclovir sensitivity; the cellular hypoxanthine phosphoribosyltransferase (HPRT) gene (Jolly et al., Proc. Nat. Acad. Sci. USA 80:477, 1983); the cellular adenine phosphoribosyltransferase (APRT) gene (Wigler et al., Proc. Natl. Acad. Sci. USA 76:1373, 1979); and bacterial cytosine deaminase, (Mullen et al., Proc. Natl. Acad. Sci. USA. 89:33, 1992).

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374–3378, 1991. Bifunctional selectable fusion genes, as described in W.I.P.O. publication WO92/08796 (published 29 May 1992) and U.S. Pat. No. 5,256,553 (issued 26 Oct. 1993), and hereby incorporated by reference, are also suitable for use in the present invention.

In addition to selectable markers, the vector RNA may also comprise other genes to be incorporated into the targeted cells. There are few constraints on including such additional sequences. Thus, numerous retroviral vector constructs have been used successfully to express foreign genes (see, e.g., Coffin, in Weiss et al. (eds.), RNA Tumor Viruses, 2nd ed., vol. 2 (Cold Spring Harbor Laboratory, N.Y., 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985). Many different gene products have been expressed using retroviral vectors. This can either be achieved by placing the sequences to be expressed under the transcriptional control of the promoter incorporated in the retroviral LTR, or by placing them under the control of a heterologous promoter inserted between the LTRs, such as the promoters described above. The presence of multiple internal promoters, initially thought to be problematic (Coffin, supra, 1985), was found to be well tolerated in several retroviral constructs (Overell et al., Mol. Cell. Biol. 8:1803, 1983). Multiple promoters, such as those described in W.I.P.O. publication WO89/03882 (published 5 May 1989), will also be useful in the present invention.

Cytokine Effector Activity of Retroviral Vectors

The viral particles bearing CTPs on their surface can be assayed for cytokine effector activity using any of a variety of known techniques, such as the well-known CTLL bioassay in which cells are incubated with $^3$H-thymidine and incorporation of radioactivity into DNA is used as a measure of cellular proliferation, as described by Gillis et al., J. Immunol. 120:2027, 1978. Other assays are described, for example, in Clemens, M. J. et al, (eds) "Lymphokines and Interferons," IRL press, Oxford, 1987, and references cited therein. In general, the CTPs of the present invention (and vectors comprising such CTPs) can simply be compared with the corresponding native cytokine for their ability to affect the target cells.

Use of Retroviral Vectors in Cell Targeting

There are many different applications in which retroviral vectors may be used as transduction agents. For example, retroviral vectors may be used to deliver a gene to a target cell which can be stably integrated into that cell in order to analyze the function of the gene and its products in the target cell, to introduce a histochemical marker into the target cell in order to monitor the fate of the cells under certain conditions, to immortalize or transform target cells by introduction of an oncogene, to enhance the expression of a gene which is poorly expressed in the target cell, to provide a copy of a gene which is missing or defective in the target cell or to insert an otherwise therapeutic gene, to modulate the growth or differentiation of the target cell, or to bring about the quiescence or death of the target cell.

Retroviral vectors can also be used as genetic tags to follow the development of a targeted sub-population. For example, several groups have followed the development of murine hematopoietic stem cells which were transduced in vitro with retroviral vectors and then transplanted into recipient mice (Williams et al., Nature 310:476, 1984; Dick et al., Cell 42:71, 1985; Keller et al., Nature 318:149, 1985). These studies have demonstrated that the infected hematopoietic cells reconstitute the hematopoietic and lymphoid tissue of the recipient animals and that the cells display a normal developmental potential in vivo. The tagged cells can be monitored using any of a number of molecular biological techniques to demonstrate the presence of the retroviral vector sequences, most notably Southern analysis and PCR (polymerase chain reaction). The ability to genetically tag cells using retroviral vectors is also useful in clinical settings in which the technique can be used to track grafts of autologous cells. This approach has already been used to track TILs (tumor-infiltrating lymphocytes) in patients given TIL therapy for terminal cancer treatment by Rosenberg et al. (N. Engl. J. Med. 323:570, 1990). The transduction of these cells with the marker gene was not associated with in vitro cellular dysfunction (Kasid et al., Proc. Nat. Acad. Sci. USA 87:473, 1990).

Suitable target cells will generally include any cells which possess the cognate receptors recognized by the CTPs. Procedures for the infection of cells, both in vitro and in vivo, are known in the art and are described, for example, in Ausubel et al. (1992), supra.

Preferred target cells include blood cells, especially lymphocytes and progenitor cells such as pluripotent lymphohematopoietic progenitor cells. Cells of the hematopoietic system are diverse in function and are of particular interest from a gene therapy standpoint. Stem and progenitor cells that give rise to mature blood cells reside principally in the bone marrow and introduction of genes into these primitive cells can give rise to long-term persistence of the inserted gene in the mature progeny cells circulating in the periphery. This has implications for the treatment of cancer, HIV infection and inherited genetic disorders. Mature T lymphocytes are also important targets for gene transfer studies, particularly in view of the key role played by T cells in controlling viral infections, auto-immune diseases and HIV infection. Specific transduction of T cells will also allow manipulation of immune disorders in vivo, by targeting T cells to either enhance T cell proliferation (using, for example, cytokines such as IL-2 or IL-4 to create an autocrine growth cycle), or to suppress T cell proliferation (using, for example, negative growth regulators, toxins or suicide genes). Finally, using the present invention, it will be possible to specifically target hematopoietic stem cells in vivo.

Using the present invention, it will be possible to target the infection event to cells present at variable or low frequencies in mixed primary cell cultures. In the case of blood cells, this will allow targeting of specific T cells in primary cell cultures, and will allow for the introduction of genes into activated T cells bearing specific receptors. Another advantageous use of the present invention will be to use a stem-cell specific receptor to target the infection event to hematopoietic stem cells in populations of mononuclear cells harvested from bone marrow or peripheral blood. Such a technology will allow transduction of the hematopoietic stem/progenitor cells without the need for cell purification, since by targeting the infection event these longer-lived cells could be transduced in the context of whole bone marrow or partially purified populations. A further application of the present invention will be the use of cell-specific targeting to transduce cells in vivo, using the retroviral vectors as an injectable gene delivery system. The specificity of infection will allow the vector to target cells bearing the cognate receptor, and will reduce or prevent the vector from infecting other cells. Targeting particular cells will not only enhance the efficiency of gene transfer but will also significantly improve the safety of such a delivery system, since the vector would transduce only the specific target cells of interest, and not all cells exposed to the virus.

The examples presented below are provided as a further guide to the practitioner of ordinary skill in the art, and are not to be construed as limiting the invention in any way.

EXAMPLE 1

Construction of Plasmid Encoding a Chimeric Targeting Protein

The vector pLXSN (Miller and Rosman, Biotechniques 7:980, 1989), part of which is shown in the schematic of FIG. 1, contains retroviral long terminal repeat (LTR) sequences, splice donor (SD) and splice acceptor (SA) sequences, and a neo gene (neo) under control of the SV40 early region promoter (SV). The plasmid DNA was digested with EcoRI and BamHI; and then the following pair of oligonucleotides were introduced by ligation in order to modify the polycloning region:

5' AAT TCC TCG AGG GTA CCG TTA ACA GAT CTG 3' SEQ ID NO:1)

5' GAT CCA GAT CTG TTA ACG GTA CCC TCG AGG 3' SEQ ID NO:2).

The resulting vector, shown as MCS-LXSN in FIG. 1, contained the following sites in the polycloning region: 5'-EcoRI-XhoI-Asp718-HpaI-BglII-BamHI-3'.

As an illustration of the preparation of a CTP, a ligand moiety was derived from a sequence encoding the cytokine IL-2, and an uptake moiety was derived from a sequence encoding the env protein of an ecotropic murine retrovirus (i.e. an "eco-env" protein). Thus, an IL-2/eco-env fusion gene was prepared comprising the following elements inserted between the 5' EcoRI site and the 3' BglII site in the polycloning region of MCS-LXSN:

1. A ligand moiety was derived from a human IL2 cDNA sequence corresponding to amino acids 1 through 133 of the published human IL-2 sequence (Taniguchi et al., Nature 302:305, 1983). A cDNA sequence encoding the human IL-2 is present in plasmid pMLSVtIL2 (which is the vector pMLSV, described by Cosman et al., Nature 312:768–771, 1984, containing the wild-type human IL-2 cDNA (as described by Taniguchi et al., supra)). The IL-2 coding sequence was obtained by polymerase chain reaction (PCR, Mullis and Faloona, Meth. Enzymol. 155:335, 1987) from plasmid pMLS-VtIL2 using the following 5' end oligonucleotide:
5'-GGC-CTG-AAT-TCG-CCG-CCA-CCA-TGT-ACA-GGA-TG-3'(SEQ ID NO:3); and the following 3' end oligonucleotide:
5'-CCA-GGA-TCC-ACC-TCC-ACC-AGT-CAG-TGT-TGA-GAT-3' (SEQ ID NO:4).

The 5' end oligo also yielded a Kozak consensus sequence, Nuc. Acid. Res. 15:3374, 1987, located upstream of the initiator methionine; and a 5' EcoRI site for cloning into the MCS-LXSN polycloning region. The 3' end oligo also yielded a sequence which upon translation would produce the following flexible peptide linker or flexon sequence (SEQ ID NO:5): -Gly-Gly-Gly-Gly-Ser- (abbreviated as Gly$_4$Ser) located at the C-terminus of the IL-2 sequence; and a 3' BamHI site to facilitate linkage to a complementary site (BglII) on the 5' end of the sequence encoding the uptake moiety.

2. An uptake moiety was derived from an ecotropic env, or "eco-env," sequence corresponding to amino acid residues 35 to 666 of the published Moloney murine leukemia virus (MoMLV) sequence (Shinnick et al., Nature 293:543–548, 1981). A cDNA sequence encoding the eco-env sequence is present in plasmid pMLV-K (Miller and Verma, J. Virol. 49:214, 1984). The eco-env coding sequence was obtained by PCR amplification of plasmid pMLV-K using the following 5' end oligo (SEQ ID NO:6):
5'-CCG-AAG-ATC-TGG-TGG-TGG-AGG-TTC-GCC-CGG-CTC-C-3'; and the following 3' end oligo (SEQ ID NO:7):
5'-TCG-CGT-AGA-TCT-CTA-GCT-ATG-GCT-CGT-A-3'.

The 5' end oligo also yielded a tandem pair of Gly$_4$Ser flexon sequences, as described above, and a BglII site to facilitate linkage to the 3' end of the ligand moiety. The 3' end oligo also yielded a termination codon and a BglII site for cloning into the MCS-LXSN polycloning region.

The resulting fragments were cloned into the polycloning region of pMCS-LXSN following routine procedures to yield the plasmid MCS-LXSN-IL2eco-env as shown in FIG. 2. DNA sequencing (Sanger et al., Proc. Natl. Acad. Sci. 74:5463, 1977) across the fusion sites confirmed the correct in-frame fusion between the IL2 sequence and gp70 sequence incorporating 3 repeats of the flexon linker between them. This vector expresses the IL2eco-env CTP under the transcriptional control of the retroviral LTR and the neo gene under the control of the SV40 early region promoter.

EXAMPLE 2

Transfection of a Packaging Cell Line

The MCS-LXSN, or MCS-LXSN-IL2eco-env plasmids were transfected into both the amphotropic packaging cell line PA317 (ATCC CRL 9078, described by Miller and Buttimore, Mol. Cell. Biol. 6:2895, 1986), and the ecotropic packaging cell line ψ2 (described by Mann, R. et al., Cell 33:153–159, 1983); using standard electroporation techniques, as previously described, for example, by Lupton et al., Mol. Cell. Biol. 11:3374, 1991 (exponentially growing cells were harvested by trypsinization, washed free of serum, and resuspended in DMEM at a concentration of $10^7$ cells/ml; supercoiled plasmid DNA (5 μg) was added to 800 μl of cell suspension ($8\times10^6$ cells), and the mixture subjected to electroporation using the Biorad Gene Pulser and Capacitance Extender (200–300 V, 960 μF, 0.4 cm electrode gap, at ambient temperature). Following transfection, the cells were returned to 9-cm dishes and grown in non-selective medium).

EXAMPLE 3

Production of Retroviral Targeting Vectors

At approximately twenty-four hours after transfection of the cells (as described in Example 2), the cell media were exchanged and, at approximately 16 hours after the exchange of media, virus particles were harvested from the cellular supernatants. The virus-containing supernatants were routinely obtained by centrifugation (at 1000×g, for 10 minutes in a bench top centrifuge) to remove viable virus producing cells and were further filtered through 0.45 μm filters to remove any smaller debris.

The PA317 supernatants were then used to infect 1×10$^6$ LGPS cells (LGPS cells express Moloney murine leukemia virus gag and pol proteins, but not envelope proteins, Miller, et al., J. Virol. 65:2220, 1991); or ψ2 cells overnight in the presence of 4 μg/ml polybrene. The ψ2 cell supernatants were used to infect 1×10$^6$ PA317 cells overnight under the same conditions. After overnight incubation with the supernatants the infected cells were placed in media containing 500 μg/ml G418. Resistant cells were grown for each vector and passaged as polyclonal cultures kept under G418 selection.

Viral supernatants were routinely harvested from polyclonal cultures of LGPS cells stably expressing MCS-LXSN and MCS-LXSN-IL2eco-env as well as from polyclonal cultures of ψ2 cells and PA317 cells stably expressing the MCS-LXSN control vector.

EXAMPLE 4

Assaying the Cytokine Effector Activity of the Retroviral Vectors

Viral supernatants derived from cells expressing the IL2eco-env CTP were assayed for their IL2 activity in the presence and absence of a polyclonal anti-human IL2 antibody (Smith et al., J. Immunol. 131:1808, 1983). IL2 biological activity was assayed by the well-known CTLL bioassay in which cells are incubated with $^3$H-thymidine and incorporation of radioactivity into DNA is used as a measure of cellular proliferation, as described by Gillis et al., J. Immunol. 120:2027, 1978. The results of this experiment are shown in Table 1.

TABLE I

IL2 activity in viral harvests derived from cell lines expressing different viral envelope proteins and IL2eco-env.

| Cell source for viral harvest | Type of envelope expressed | IL2 activity no antibody present (unit/ml) | IL2 activity in presence of anti-IL2 antibody (unit/ml) |
|---|---|---|---|
| ψ2 MCS-LXSN Mixed culture | ecotropic | 0 | 0 |
| PA317 MCS-LXSN Mixed culture | amphotropic | 0 | 0 |
| LGPS MCS-LXSN Mixed culture | none | 0 | 0 |
| LGPS MCS-LXSN-IL2eco-env Mixed culture | IL2eco-env | 457 | 0 |

These data demonstrate that there was no endogenous IL2 activity associated with the normal ecotropic envelope protein (ψ2 cells), with the amphotropic envelope protein (PA317 cells), nor with the LGPS cells. In contrast, the LGPS cells expressing the MCS-LXSN-IL2eco-env protein did exhibit IL2 activity, confirming that the IL2 molecule fused to the ecotropic gp70 was biologically active and was properly processed to the cell surface of the expressing cells.

The observation that IL2 activity was neutralizable by the anti-human IL2 antibody confirmed that the activity observed was that of authentic human IL-2.

EXAMPLE 5

Uptake and Expression of the Retroviral Vectors

Retroviral supernatants were harvested from polyclonal cultures of ψ2, PA317 and LGPS cells stably expressing the MCS-LXSN control vector as well as from polyclonal cultures of LGPS cells stably expressing the MCS-LXSN-IL2eco-env vector. These supernatants were titered on NIH/3T3 cells, with the addition of anti-(human IL-2) antibody to a duplicate set of infections, as follows. Exponentially dividing NIH/3T3 cells were removed from the culture dishes with trypsin-EDTA (Gibco) and seeded at a density of 2.5×10$^4$ per 35 mm tissue culture well (Costar). After 24 h of incubation, the medium was aspirated and replaced with serial dilutions of virus-containing supernatant (1ml/well) in medium containing Polybrene (4 μg/ml) (Sigma Chemical Co.). All supernatants were centrifuged at 2,000 rpm for 10 min. before use to remove viable cells. Cells were incubated with the virus overnight, and then the supernatant was aspirated and replaced with fresh growth medium. Cells were selected for drug resistance after a further 24 h of growth by adding G418 (Gibco) to a final concentration of 500 μg/ml. Cells were incubated for 7 days and then refed with drug-containing medium. After a total of 12 to 14 days of growth, cells were fixed with 100% methanol and stained with methylene blue.

Figure 3:
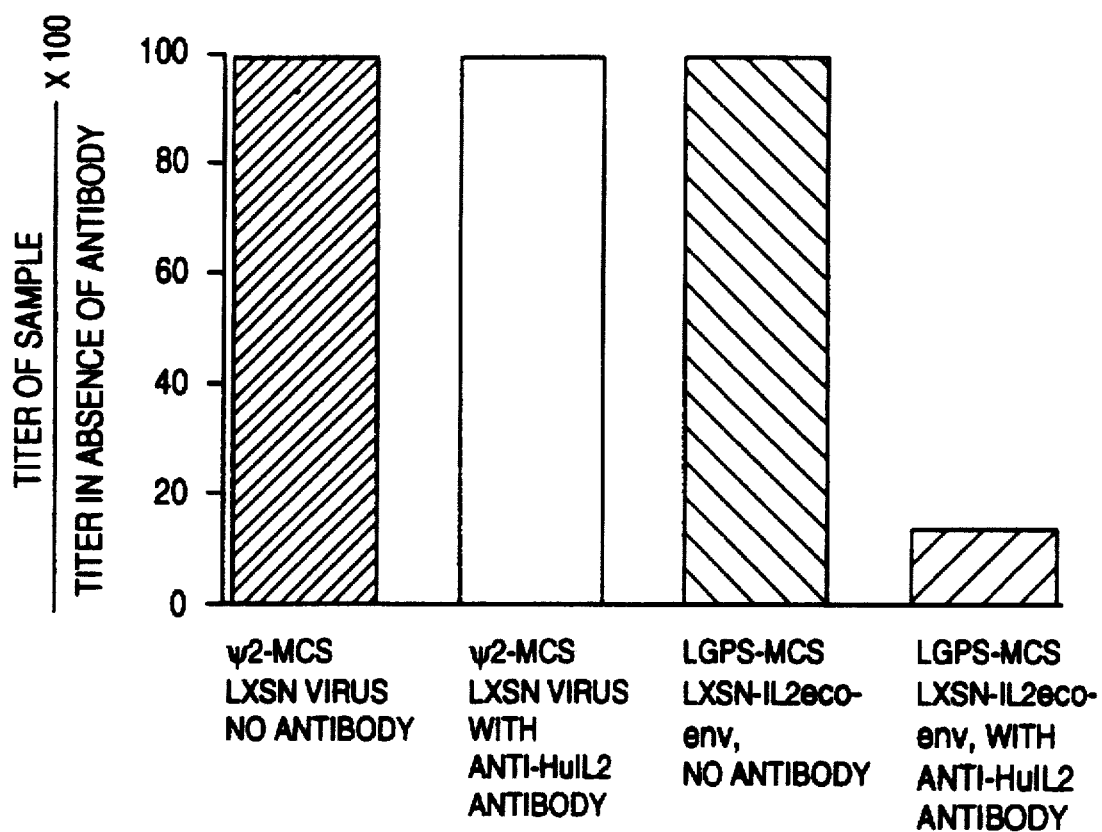
FIG. 3 shows the effect of a rabbit anti-(human IL2) polyclonal antibody on infection of NIH/3T3 cells with virus derived from ψ2 cells expressing the ecotropic-enveloped virus (ψ2-MCS-LXSN) or LGPS cells expressing the CTP-enveloped virus (LGPS-MCS-LXSN-IL2eco-env).
Figure 4:
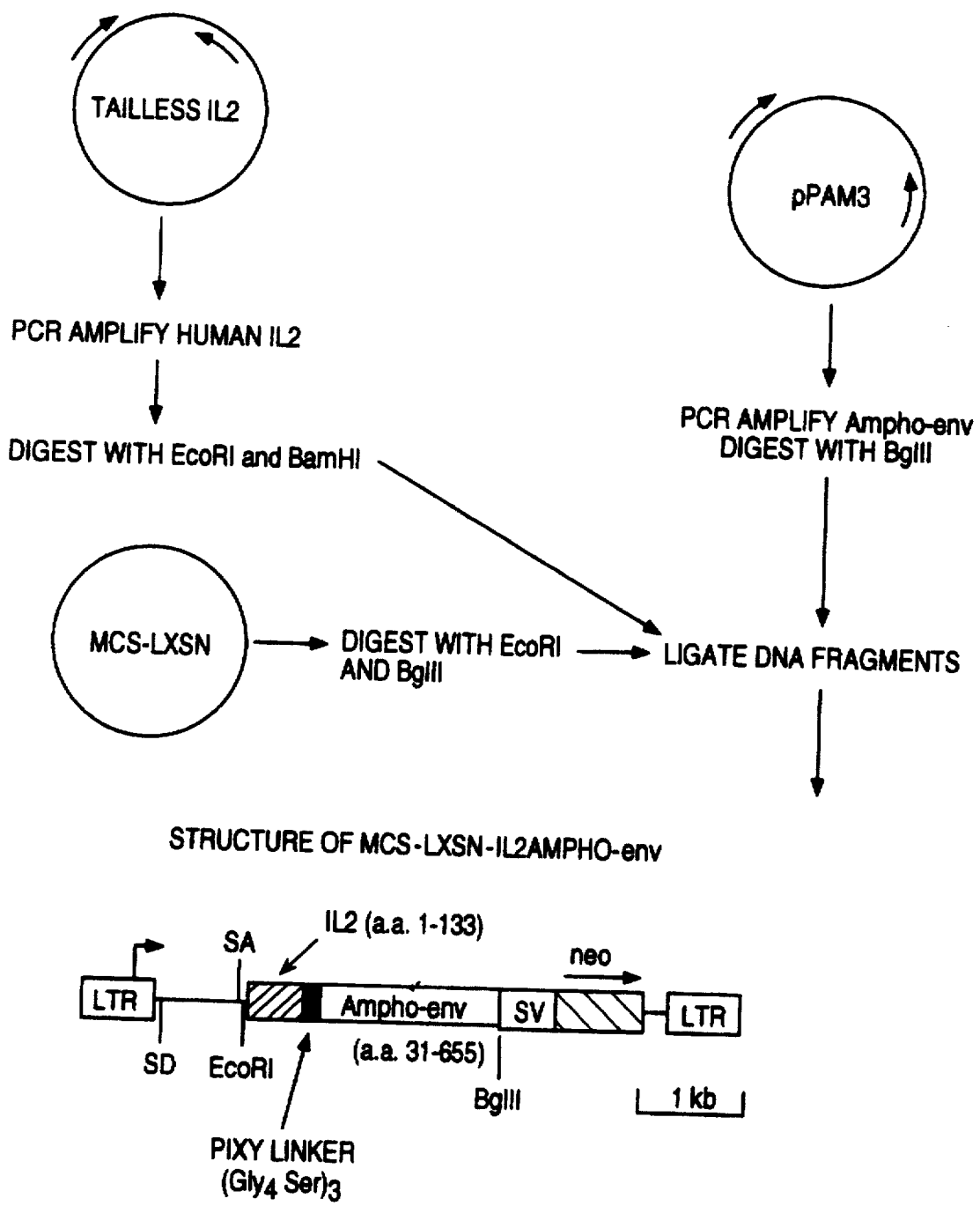
FIG. 4 is a schematic diagram showing the construction of the MCS-LXSN-IL2ampho-env retroviral vector, where the sequence encoding the CTP (the IL2ampho-env sequence) was inserted between the EcoRI and BglII sites of the MCS-LXSN vector.

FIG. 3 shows the effect of the rabbit anti-(human IL2) polyclonal antibody on infection of NIH/3T3 cells with virus derived from ψ2 cells expressing the ecotropic-enveloped virus (ψ2-MCS-LXSN) or LGPS cells expressing the CTP-enveloped virus (LGPS-MCS-LXSN-IL2eco-env). The data demonstrate that the antibody had no effect on infection by the ecotropic-enveloped virus, but caused 87% inhibition of infection by the CTP-enveloped virus; confirming that the IL2eco-env CTP had the capacity to infect cells through its envelope component and was functional in the context of a fusion with human IL2. Infections with viral particles derived from the LGPS cells expressing MCS-LXSN exhibited no titer, as expected from a cell which does not express an envelope protein. In the presence of anti-IL2 antibody, infections with virus derived from ψ2 cells were unaffected, but infections using the IL2eco-env protein were strongly inhibited. These data show that the anti-IL2 antibody can bind to the IL2eco-env CTP and can conformationally or sterically interfere with the binding of the envelope component to its receptor, in contrast to the wild-type envelope proteins expressed by the ψ2 cells. In addition, the data suggest that the IL2eco-env CTP was properly processed and incorporated into the retroviral particles produced by LGPS cells in a manner analogous to the native envelope proteins. The data thus indicated that the IL2eco-env CTP was displayed on the surface of the viral particle, that the env portion of the molecule (i.e. the uptake moiety) was functional in mediating virus entry, that the IL-2 portion of the molecule (i.e. the ligand moiety) was biologically active in a functional assay for cytokine, and that the protein expressed was indeed a fusion molecule, since anti-IL-2 antibody specifically inhibited infection by the particles bearing the IL2eco-env fusion. Since the transformed cells exhibited resistance to G418, which required expression of the n gene, the data also demonstrated the successful expression of vector nucleic acid in cells infected with a retroviral targeting vector of the present invention.

EXAMPLE 6

Construction of Another Plasmid Encoding a Chimeric Targeting Protein

As another illustration of the preparation of a CTP, a ligand moiety was derived from a sequence encoding the cytokine IL-2, and an uptake moiety was derived from a sequence encoding the env protein of an amphotropic murine retrovirus (i.e. an "ampho-env" protein). Thus, an IL-2/ampho-env fusion gene was prepared comprising the following elements inserted between the 5' EcoRI site and the 3' BglII site in the polycloning region of MCS-LXSN:

1. A ligand moiety was derived from a human IL2 cDNA sequence as described in Example 1.
2. An uptake moiety was derived from an amphotropic env, or "ampho-env," sequence corresponding to amino acid residues 31 to 665 of the published 4070A amphotropic murine leukemia virus sequence (Ott et al., J. Virol. 64:757–766, 1990). A cDNA sequence encoding the ampho-env sequence is present in plasmid pPAM3 (Miller and Buttimore, Mol. Cell. Biol. 6:2895–2902, 1986). The ampho-env coding sequence was obtained by PCR amplification of plasmid pPAM3 using the following 5' end oligo:

5'-GGC-CAA-GAT-CTG-GTG-GTG-GAG-GTT-CAG-GAG-GAG-GTG-GTT-CAA-TGG-CAG-AGA-GC-3'; and the following 3' end oligo: 5'-TCG-CGT-AGA-TCT-CTA-GTC-ATG-GCT-C-3'.

The 5' end oligo also yielded a tandem pair of flexon sequences, as described in Example 1, and a BglII site to facilitate linkage to the 3' end of the ligand moiety. The 3' end oligo also yielded a termination codon and a BglII site for cloning into the MCS-LXSN polycloning region.

The resulting fragments were cloned into the polycloning region of pMCS-LXSN following routine procedures to yield the plasmid MCS-LXSN-IL2ampho-env. DNA sequencing (Sanger et al., Proc. Natl. Acad. Sci. 74:5463, 1977) across the fusion sites confirmed the correct in-frame fusion between the IL2 sequence and the amphotropic env sequence incorporating 3 repeats of the flexon linker between them. This vector expresses the IL2ampho-env CTP under the transcriptional control of the retroviral LTR and the neo gene under the control of the SV40 early region promoter.

Transfection of MCS-LXSN or MCS-LXSN-IL2ampho-env into packaging cell lines was carried out as described in Example 2, above.

Production of retroviral targeting vectors comprising the ampho-env CTPs was carried out as described in Example 3, above.

As described in Example 3, viral supernatants were routinely harvested from polyclonal cultures of LGPS cells stably expressing MCS-LXSN and MCS-LXSN-IL2ampho-env as well as from polyclonal cultures of ψ2 cells and PA317 cells stably expressing the MCS-LXSN control vector.

EXAMPLE 7

Assaying the Cytokine Effector Activity of the Retroviral Vectors

Viral supernatants of Example 6, including those derived from cells expressing the MCS-LXSN-IL2ampho-env protein, were assayed for their IL2 activity in the presence and absence of a polyclonal anti-human IL antibody (Smith et al., J. Immunol. 131:1808, 1983). IL2 biological activity was assayed by the CTLL bioassay as described in Example 4. The results of this experiment are shown in Table 2.

TABLE 2

IL2 activity in viral harvests derived from cell lines expressing different viral envelope proteins and IL2ampho-env.

| Cell source for viral harvest | Type of envelope expressed | IL2 activity no antibody present (unit/ml) | IL2 activity in presence of anti-IL2 antibody (unit/ml) |
|---|---|---|---|
| ψ2 MCS-LXSN Mixed culture | ecotropic | 0 | 0 |
| PA317 MCS-LXSN Mixed culture | amphotropic | 0 | 0 |
| LGPS MCS-LXSN Mixed culture | none | 0 | 0 |
| LGPS MCS-LXSN-IL2ampho-env Mixed culture | IL2ampho-env | 502 | 0 |

These data demonstrate that there was no endogenous IL2 activity associated with the normal ecotropic envelope protein (ψ2 cells), with the amphotropic envelope protein (PA317 cells), nor with the LGPS cells. In contrast, the LGPS cells expressing the MCS-LXSN-IL2ampho-env protein did exhibit IL2 activity, confirming that the IL2 molecule fused to an amphotropic env protein was biologically active and was properly processed to the cell surface of the expressing cells. The observation that IL2 activity was neutralizable by the anti-(human IL2) antibody confirmed that the activity observed was that of authentic human IL2.

EXAMPLE 8

Update and Expression of the Retroviral Vectors

Figure 5:
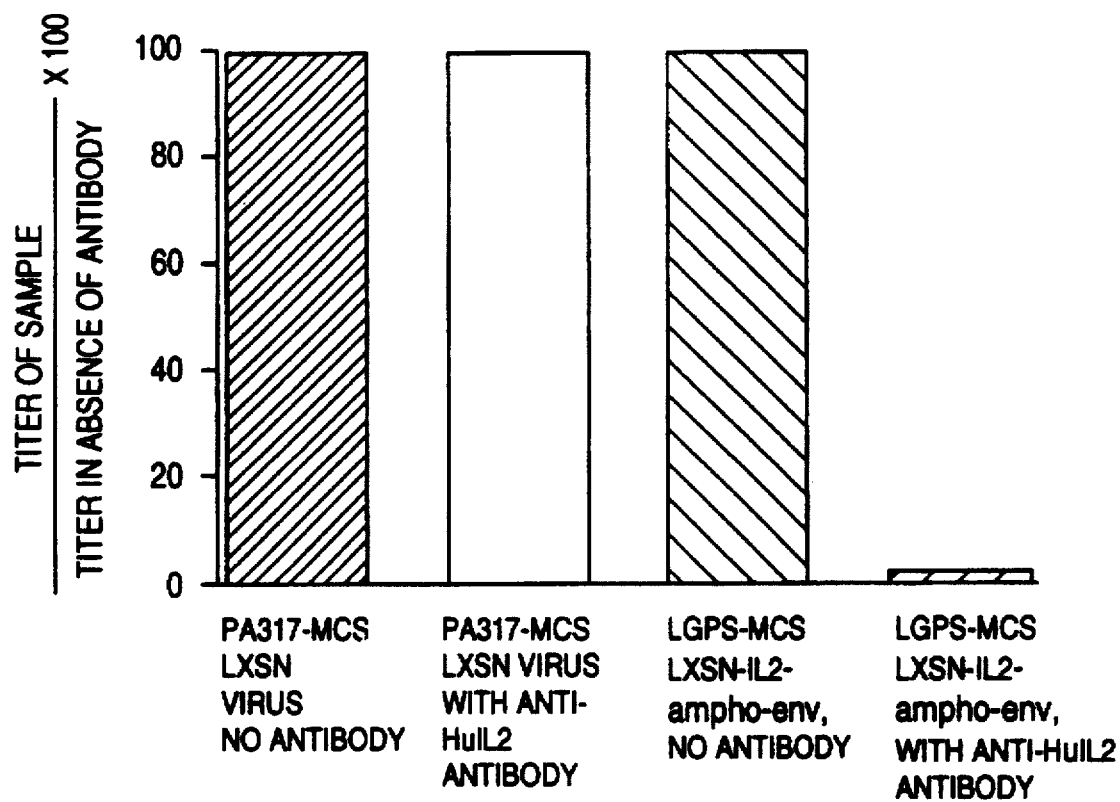
FIG. 5 shows the effect of a rabbit anti-(human IL2) polyclonal antibody on infection of NIH/3T3 cells with virus derived from PA317 cells expressing the amphotropic-enveloped virus (PA317-MCS-LXSN) or LGPS cells expressing the CTP enveloped virus (LGPS-MCS-LXSN-IL2ampho-env).

The ability of the ampho-IL2 CTP to infect NIH/3T3 cells was evaluated by following the approach described in Example 5. These results are shown in FIG. 5. The results show a 100% inhibition of infection when anti-human IL2 antibody was present with the ampho-IL2 retroviral targeting vector, but no inhibition of the PA317 virus which has the amphotropic envelope protein only.

We claim:

1. A chimeric targeting protein for cell targeting of a retroviral vector, wherein the chimeric targeting protein comprises a ligand moiety which binds to a receptor on a target cell, wherein the ligand moiety is a cytokine or an analog thereof which contains at least that portion of a cytokine polypeptide required for binding to receptors for the cytokine on the surface of mammalian cells, and an uptake moiety which mediates entry of said vector into the target cell, wherein the uptake moiety is a viral envelope protein or an analog thereof which contains at least that portion of a viral envelope protein required for anchoring the viral envelope protein to the virus surface.

2. The chimeric targeting protein of claim 1, wherein the cytokine is an interleukin.

3. The chimeric targeting protein of claim 2, wherein the cytokine is IL-2.

4. The chimeric targeting protein of claim 1, wherein the cytokine is a CSF-type cytokine.

5. The chimeric targeting protein of claim 1, wherein the cytokine is a chemotactic factor.

6. The chimeric targeting protein of claim 1, wherein the cytokine is an interferon.

7. The chimeric targeting protein of claim 1, wherein the cytokine is a growth factor.

8. The chimeric targeting protein of claim 1, wherein the cytokine is a TGF-β-type cytokine.

9. The chimeric targeting protein of claim 1, wherein the cytokine is an intercrine cytokine.

10. The chimeric targeting protein of claim 1, wherein the cytokine binds to a receptor on a lymphohematopoietic progenitor cell.

11. The chimeric targeting protein of claim 1, wherein the cytokine is an analog of flk-2 ligand which binds to flk-2.

12. The chimeric targeting protein of claim 1, wherein the cytokine binds to a Type-I cytokine receptor on a target cell.

13. The chimeric targeting protein of claim 1, wherein the cytokine binds to a Type-II cytokine receptor on a target cell.

14. The chimeric targeting protein of claim 1, wherein the cytokine binds to a Type-III cytokine receptor on a target cell.

15. The chimeric targeting protein of claim 1, wherein the cytokine binds to a Type-IV cytokine receptor on a target cell.

16. The chimeric targeting protein of claim 1, further comprising a flexon.

17. The chimeric targeting protein of claim 16, wherein the flexon is located between the ligand moiety and the uptake moiety.

18. The chimeric targeting protein of claim 1, wherein the viral envelope protein is a C-type retroviral envelope protein.

19. The chimeric targeting protein of claim 1, wherein the viral envelope protein is an amphotropic retroviral envelope protein.

20. The chimeric targeting protein of claim 1, wherein the viral envelope protein is an ecotropic retroviral envelope protein.

21. The chimeric targeting protein of claim 1, wherein the viral envelope protein is the envelope protein of at murine leukemia virus.

22. A polynucleotide encoding the chimeric targeting protein of claim 1.

23. The polynucleotide of claim 22, wherein the polynucleotide comprises an in-frame fusion of a nucleic acid sequence encoding a ligand moiety with a nucleic acid sequence encoding an uptake moiety.

24. A method of preparing a polynucleotide encoding a chimeric targeting protein, said method comprising providing a first polynucleotide comprising a nucleic acid sequence encoding a ligand moiety consisting of a cytokine or analog thereof, and providing a second polynucleotide comprising a nucleic acid sequence encoding an uptake moiety consisting of a viral envelope protein or analog thereof, and ligating said first polynucleotide to said second polynucleotide such that said ligation results in a polynucleotide encoding a chimeric targeting protein, wherein the chimeric targeting protein comprises a ligand moiety which binds to a receptor on a target cell, wherein the ligand moiety is a cytokine or an analog thereof which contains at least that portion of a cytokine polypeptide required for binding to receptors for the cytokine on the surface of mammalian cells, and an uptake moiety which mediates entry of said vector into the target cell, wherein the uptake moiety is a viral envelope protein or an analog thereof which contains at least that portion of a viral envelope protein required for anchoring the viral envelope protein to the virus surface.

25. A retroviral targeting vector comprising the chimeric targeting protein of claim 1.

26. The retroviral targeting vector of claim 25, wherein the chimeric targeting protein causes cytokine effector activity.

27. A packaging cell line which produces retroviral targeting vectors according to claim 25.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:

( A ) LENGTH: 30 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1:

AATTCCTCGA GGGTACCGTT AACAGATCTG                                                30

( 2 ) INFORMATION FOR SEQ ID NO:2:

( i ) SEQUENCE CHARACTERISTICS:
                    ( A ) LENGTH: 30 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2:

GATCCAGATC TGTTAACGGT ACCCTCGAGG                                                30

( 2 ) INFORMATION FOR SEQ ID NO:3:

( i ) SEQUENCE CHARACTERISTICS:
                    ( A ) LENGTH: 32 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:3:

GGCCTGAATT CGCCGCCACC ATGTACAGGA TG                                             32

( 2 ) INFORMATION FOR SEQ ID NO:4:

( i ) SEQUENCE CHARACTERISTICS:
                    ( A ) LENGTH: 33 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:4:

CCAGGATCCA CCTCCACCAG TCAGTGTTGA GAT                                            33

( 2 ) INFORMATION FOR SEQ ID NO:5:

( i ) SEQUENCE CHARACTERISTICS:
                    ( A ) LENGTH: 5 amino acids
                    ( B ) TYPE: amino acid
                    ( C ) STRANDEDNESS: single
                    ( D ) TOPOLOGY: linear ( x i ) SEQUENCE DESCRIPTION: SEQ ID NO:5:

Gly Gly Gly Gly Ser
        1               5

( 2 ) INFORMATION FOR SEQ ID NO:6:

( i ) SEQUENCE CHARACTERISTICS:
                    ( A ) LENGTH: 34 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:6:

CCGAAGATCT GGTGGTGGAG GTTCGCCCGG CTCC                                           34

( 2 ) INFORMATION FOR SEQ ID NO:7:

( i ) SEQUENCE CHARACTERISTICS:
                    ( A ) LENGTH: 28 base pairs (B) TYPE: nucleic acid
(C) STRANDEDNESS: single
(D) TOPOLOGY: linear (xi) SEQUENCE DESCRIPTION: SEQ ID NO:7:

TCGCGTAGAT CTCTAGCTAT GGCTCGTA                    28